US006303370B1

(12) United States Patent
Kappen et al.

(10) Patent No.: US 6,303,370 B1
(45) **Date of Patent: *Oct. 16, 2001**

(54) TISSUE-SPECIFIC REGULATORY ELEMENTS

(75) Inventors: Claudia Kappen, Scottsdale, AZ (US); Paul J. Yaworsky, Rockland, MA (US)

(73) Assignee: Mayo Foundation for Medical Education and Research, Rochester, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/047,031

(22) Filed: Mar. 24, 1998

(51) Int. Cl.[7] .............................. C12N 15/00; C12N 5/00; C07H 21/02; C07H 21/04

(52) U.S. Cl. ........................ 435/320.1; 435/325; 435/368; 536/23.1; 536/24.1

(58) Field of Search ....................... 800/8, 18; 435/320.1, 435/325, 368; 536/23.1, 24.1

(56) References Cited

U.S. PATENT DOCUMENTS 5,338,839 * 8/1994 Mckay et al. ........................ 536/235

OTHER PUBLICATIONS

Zimmerman et al. Neuron. 12:11–24, 1994.*

Lothian et al. Euro. J. Neurosci. 9:452–462, 1997.*

Dahlstrand J, et al., Nestin mRNA expression correlates with the central nervous system progenitor cell state in many, but not all, regions of developing central nervous system, *Dev. Brain Res.* 84:109–129 (1995).

Dahlstrand J et al., Characterization of the human nestin gene reveals a close evolutionary relationship to neurofilaments, *J. Cell Sci.* 103:589–597 (1992).

Dahlstrand J et al., Expression of the class VI intermediate filament nestin in human central nervous system tumors *Cancer Res.* 52:5334–5341 (1992).

Frederiksen K and RDG McKay, Proliferation and differentiation of rat neuroepithelial precursor cells in vivo, *J. Neurosci.* 8:1144–1151 (1988).

Frisén J et al.,. Rapid, widespread, and longlasting induction of nestin contributes to the generation of glial scar tissue after CNS injury, *J. Cell Biol.* 131:453–464 (1995).

Fröjdman K et al., The intermediate filament protein nestin occurs transiently in differentiating testis of rat and mouse, *Differentiation* 61:243–249 (1997).

Gossler A et al., Mouse embryonic stem cells an reporter constructs to detect developmentally regulated genes, *Science* 244:463–465 (1989).

Gossler A and J Zachgo, In: Gene targeting: a practical approach., Gene enhancer trap screens in ES cell chimeras, Ed. AL Joyner, IRL Press, Oxford, NY, Tokyo, pp. 181–227 (1993) (best copy available).

Hockfield S and RDG McKay, Identification of major cell classes in the developing mammalian nervous system, *J. Neurosci.* 5:3310–3328 (1985).

Josephson R et al. CNS–specific expression of nestin requires a complex enhancer bound by the POU domain factors BRN–1 and BRN–2, Abstract 562.7 at Society of Neuroscience, vol. 23 (1997).

Kachinsky AM et al., Intermediate filaments in cardiac myogenesis: Nestin in the developing mouse heart, *J. Histochem. Cytochem.* 43:843–847 (1995).

Kachinsky AM et al., Myogenesis and the intermediate filament protein, nestin, *Dev. Biol.* 165:216–228 (1994).

Lardelli M et al., Expression of the Notch 3 intracellular domain in mouse central nervous system progenitor cells is lethal and leads to disturbed neural tube development, *Mech. Dev.* 59:177–190 (1996).

Lee MK and DW Cleveland, Neuronal intermediate filaments, *Annu. Rev. Neurosci.* 19:187–217 (1996).

Lendahl U et al., CNS stem cells express a new class of intermediate filament protein, *Cell* 60:585–595 (1990).

Li P et al., Spacing and orientation of bipartite DNA–binding motifs as potential functional determinants for POU domain factors, *Genes and Dev.* 7:2483–2496 (1993).

Lothian C and U Lendahl, An evolutionarily conserved region in the second intron of the human nestin gene directs gene expression to CNS progenitor cells and to early neural crest cells, *Eur. J. Neurosci.* 9:452–462 (1997).

Mandel G and D McKinnon, Molecular basis of neural–specific gene expression, *Annu Rev Neurosci.* 16:323–345 (1993).

Marks MC et al., H–2RIIBP (RXR β) heterodimerization provides a mechanism for combinatorial diversity in the regulation of retinoic acid and thyroid hormone responsive genes, *EMBO J.* 11:1419–1435 (1992).

(List continued on next page.)

*Primary Examiner*—Deborah J. R. Clark
*Assistant Examiner*—Sumesh Kaushal
(74) *Attorney, Agent, or Firm*—Fish & Richardson P.C. P.A.

(57) ABSTRACT

The invention provides methods and materials related to the regulation of nucleic acid expression. Specifically, the invention provides midbrain-specific and NS-specific regulatory elements as well as regulatory elements that potentiate nucleic acid expression and regulatory elements that cooperate with other regulatory elements. In addition, the invention provides temporal regulatory elements that regulate nucleic acid expression in a temporal manner. Further, the invention provides nucleic acid constructs that contain these regulatory elements in combination with selected nucleic acid sequences. The invention also provides cells and animals that contain these regulatory elements and constructs as well as methods of providing an animal with a selected nucleic acid sequence that is expressed in a tissue-specific or temporal manner.

17 Claims, 8 Drawing Sheets

OTHER PUBLICATIONS

Peers B et al., Regulatory elements controlling pituitary–specific expression of the human prolactin gene, *Mol. Cell Biol.* 10:4690–4700 (1990).

Reynolds BA and S Weiss, Generation of neurons and astrocytes from isolated cells of the adult mammalian central nervous system, *Science* 255:1707–1710 (1992).

Ringstedt T et al., Limb proprioceptive deficits without neuronal loss in transgenic mice overexpressing neurotrophin–3 in the developing nervous system, *Development* 124:2603–2613 (1997).

Sejersen T and U Lendahl, Transient expression of the intermediate filament nestin during skeletal muscle development, *J. Cell Sci.* 106:1291–1300 (1993).

Stemple DL and DJ Anderson, Isolation of a stem cell for neurons and glia from the mammalian neural crest, *Cell* 71:973–985 (1992).

Terling C et al., Expression of the intermediate filament nestin during rodent tooth development, *Int. J. Dev. Biol.* 39:947–956 (1995).

Tohyama T et al., Nestin expression in embryonic human neuroepithelium and in human neuroepithelial tumor cells, *Lab. invest.* 66:303–312 (1992).

Williams BP and J Price, Evidence for multiple precursor cell types in the embryonic rat cerebral cortex, *Neuron*, 14:1181–1188 (1995).

Yaworksy PJ et al., Transgenic analyses reveal developmentally regulated neuron– and muscle–specific elements in the murine neurofilament light chain gene promoter, *J. Biol. Chem.* 272:25112–25120 (1997).

Zimmerman LB et al., Independent regulatory elements in the nestin gene direct transgene expression to neural stem cells or muscle precursors, *Neuron* 12:11–24 (1994).

* cited by examiner

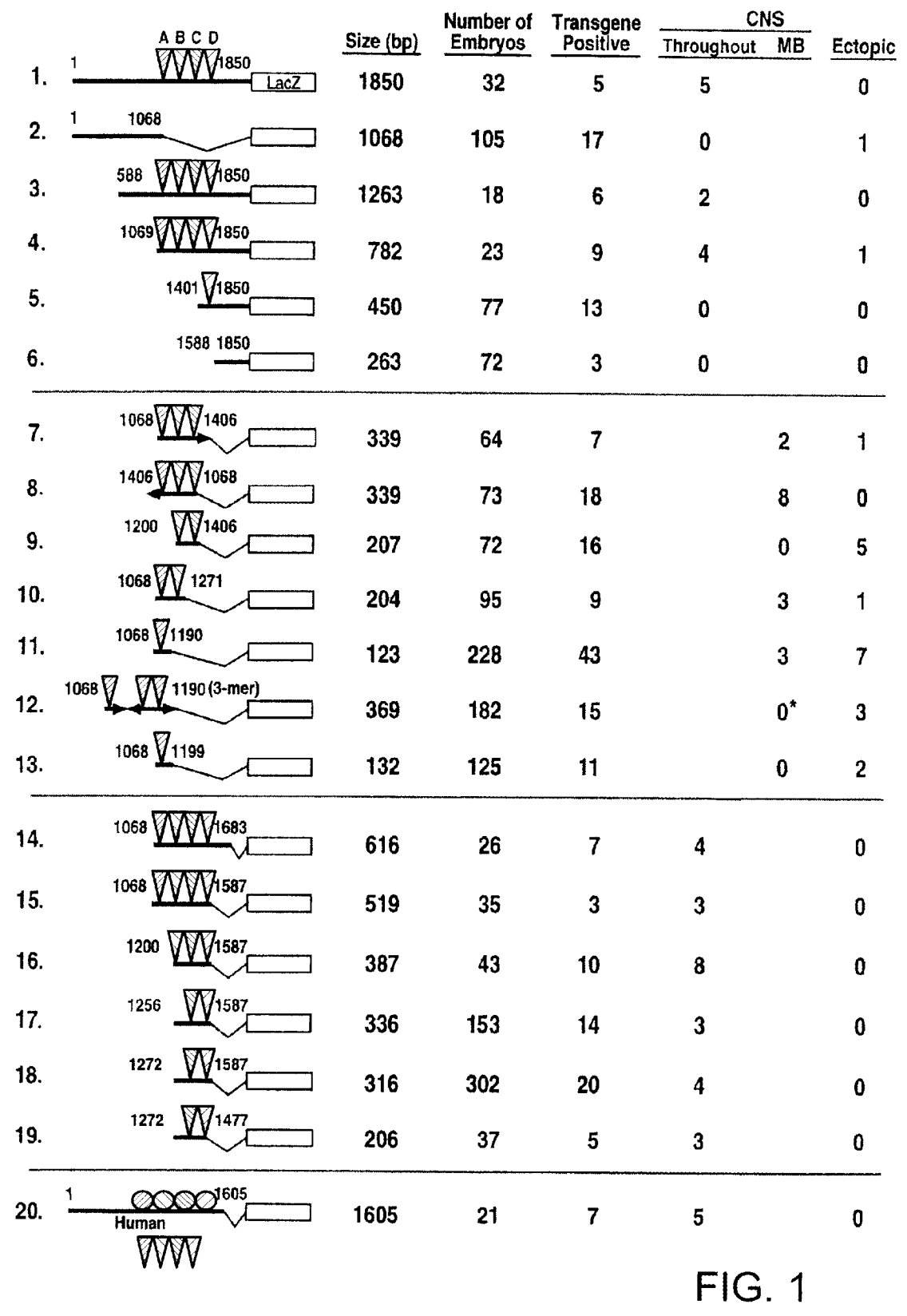

| | Construct | Size (bp) | Number of Embryos | Transgene Positive | CNS Throughout | CNS MB | Ectopic |
|---|---|---|---|---|---|---|---|
| 1. | A B C D; 1–1850; LacZ | 1850 | 32 | 5 | 5 | | 0 |
| 2. | 1–1068 | 1068 | 105 | 17 | 0 | | 1 |
| 3. | 588–1850 | 1263 | 18 | 6 | 2 | | 0 |
| 4. | 1069–1850 | 782 | 23 | 9 | 4 | | 1 |
| 5. | 1401–1850 | 450 | 77 | 13 | 0 | | 0 |
| 6. | 1588 1850 | 263 | 72 | 3 | 0 | | 0 |
| 7. | 1068–1406 | 339 | 64 | 7 | | 2 | 1 |
| 8. | 1406–1068 | 339 | 73 | 18 | | 8 | 0 |
| 9. | 1200–1406 | 207 | 72 | 16 | | 0 | 5 |
| 10. | 1068–1271 | 204 | 95 | 9 | | 3 | 1 |
| 11. | 1068–1190 | 123 | 228 | 43 | | 3 | 7 |
| 12. | 1068–1190 (3-mer) | 369 | 182 | 15 | | 0* | 3 |
| 13. | 1068–1199 | 132 | 125 | 11 | | 0 | 2 |
| 14. | 1068–1683 | 616 | 26 | 7 | 4 | | 0 |
| 15. | 1068–1587 | 519 | 35 | 3 | 3 | | 0 |
| 16. | 1200–1587 | 387 | 43 | 10 | 8 | | 0 |
| 17. | 1256–1587 | 336 | 153 | 14 | 3 | | 0 |
| 18. | 1272–1587 | 316 | 302 | 20 | 4 | | 0 |
| 19. | 1272–1477 | 206 | 37 | 5 | 3 | | 0 |
| 20. | 1–1605 Human | 1605 | 21 | 7 | 5 | | 0 |

FIG. 1

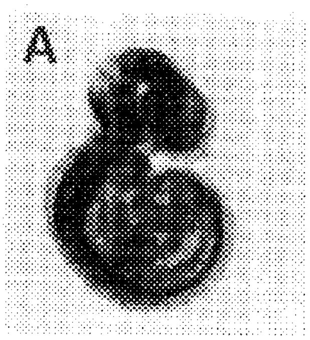
FIG. 2A
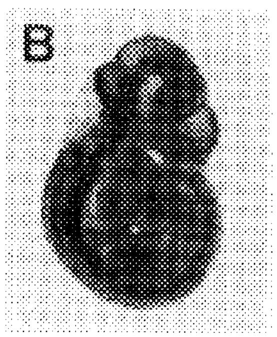
FIG. 2B
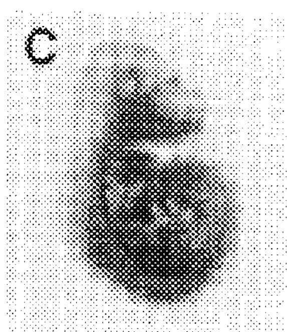
FIG. 2C
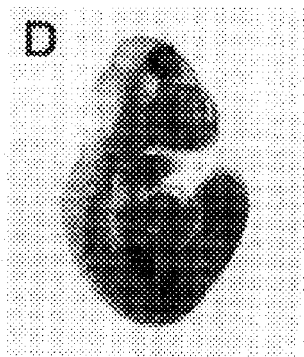
FIG. 2D
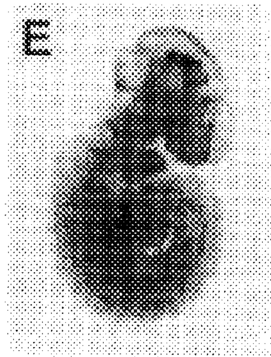
FIG. 2E
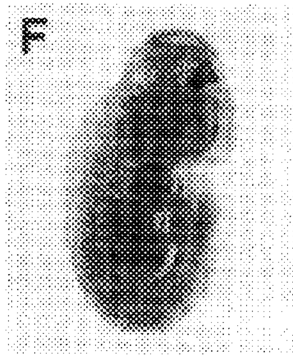
FIG. 2F
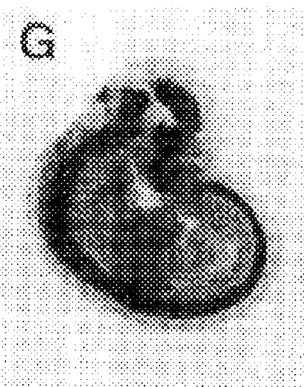
FIG. 2G
H
FIG. 2H
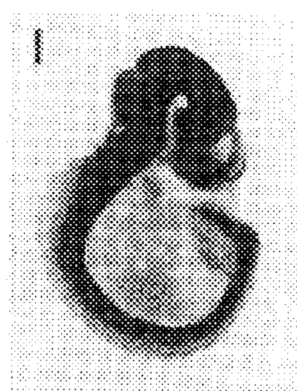
FIG. 2I

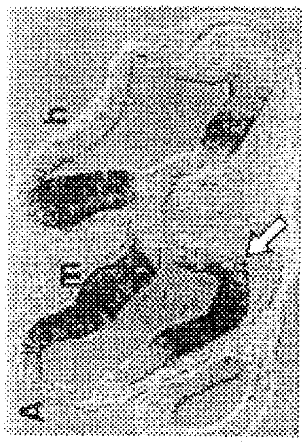
FIG. 3A
FIG. 3B
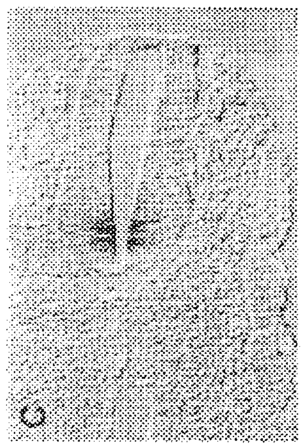
FIG. 3C
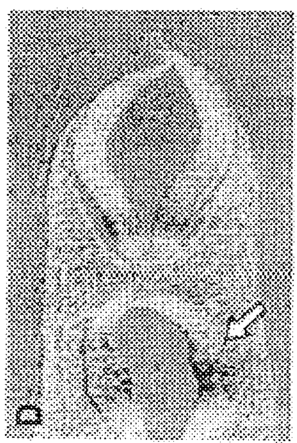
FIG. 3D
FIG. 3E
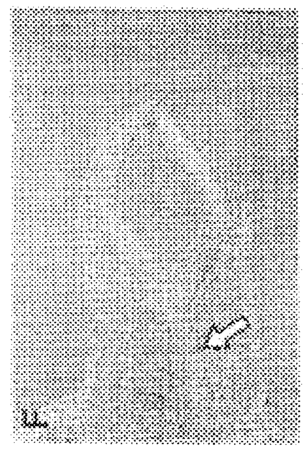
FIG. 3F
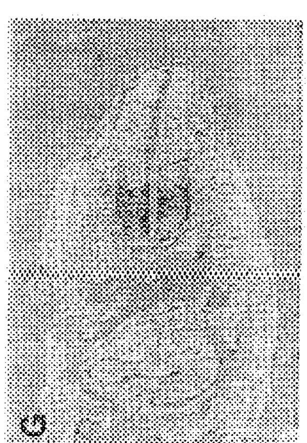
FIG. 3G
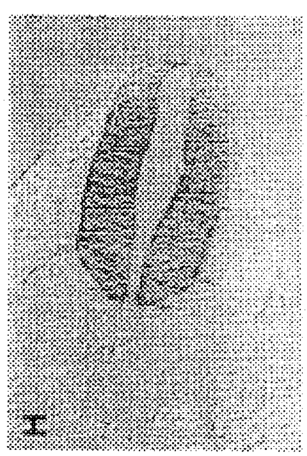
FIG. 3H
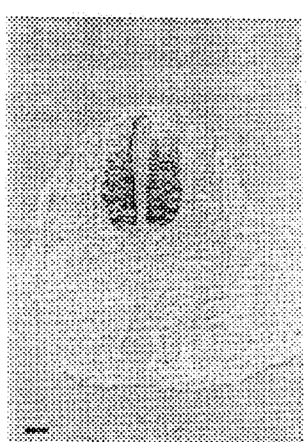
FIG. 3I

```
RAT    1068 ACTAGTTCCGAATCCCATG....TGAACTGATT..TCCCTCATCTCCTTC 1111
HUMAN   940 AGCAGCTGCTCATCCTAAGTTATTGAATTGATTGGTCCCTGCTCCCCT.. 987

       1112 AATCAGCTCCATAGGCCACTGAGGCAGGGCCATGAACGTTAAGACCTC.. 1159
        988 .CTTTGGTTCAAGGGGCGCTGAGGAAGGGGCCTGGACACAAAGACCTCTG 1036
                                                   RXR-β
       1160 TGCCCTGAAGAG.................TTTGTGATCCTGAGATGAGGG 1192
       1037 TGCCCCGAAGAGCTTGGGATCCAGAGTGCTTAGAGATCCTGAGATGAGGG 1086

       1193 .CTTTAGCCCCAGTCAGTCCTCTGAGGGGAAGGGTCCAGGCAGCTCTGAG 1241
       1087 CCCTGACCCCCAGTGAAGCCACCGAGGGGAAGGGTCTGGTGGCCCCGAG 1136

       1242 GAATGTAACCACTGGCGTTTGAGGTCTGAA 1271
       1137 GAATTTAACTGCTATTTTTTGAGGCATGAA 1166
```

FIG. 4B

```
RAT   1272 AAGGATTTGGAGAAGGGGAG 1291
HUMAN 1167 AAGGATTTGGAGAGGGGGAG 1189

1292 CTGAATTCATTTGCTTTTGTCTGTTACCAGCTCTGGGGGC.......... 1331
1187 CTGAATTCATTTGCTTTTGTCTGTCGCTAGCTCTGGGGGCCACCGGGGAA 1236
     Pit-1

1332 ...AGAGAGAGAGCCATCCCCTGGGAACAGCCTGAGAATTCCCACTTCCC 1378
1237 GGAGGAGGGAG.CCCATCCCATGGGAACGGCCTGAGAATTCCCACTTCCC 1285

1379 CTGAGG.GCCCTCCCTTCTTAGGCCCTCCAGATGGTAGTGTGGACAAAAG 1428
1286 C..AGA.TCCTCTCCTTCTCAGACCCTCCAGATGGTGGCTTGGAC.AATG 1332

1429 GCAATAATTAGCATGAGAATCGGCCTCCCTCCCAGAGGATGAGGTCATC 1477
1333 GCAGCAATTAGCATGAGAATCGGTCCCCCACACAGAGGATGAGGTGATT 1381
          POU-classIII                        RXR-β
```

FIG. 4C

TISSUE-SPECIFIC REGULATORY ELEMENTS

BACKGROUND

1. Technical Field

The invention relates to methods and materials involved in the tissue-specific regulation of nucleic acid expression.

2. Background Information

Two components help determine cell-specific nucleic acid and polypeptide expression: transcription factors and regulatory elements. Transcription factors are polypeptides that bind nucleic acid sequences, whereas regulatory elements are specific nucleic acid sequences, usually located near a gene, that are bound by transcription factors. It is the binding of a transcription factor to a regulatory element that typically stimulates transcription of a nearby gene. Thus, the transcription factors available within a cell determine which nucleic acids and polypeptides are expressed by that cell. For example, brain cells contain a set of transcription factors that are unique to brain cells. This set of transcription factors stimulates transcription of brain-specific polypeptides since genes that encode brain-specific polypeptides have nearby regulatory elements that are recognized by transcription factors present within brain cells. Non-brain-specific genes, however, do not have nearby regulatory elements that could be recognized by transcription factors present within brain cells and thus are not expressed. Likewise, non-brain cells do not contain the same set of transcription factors and thus do not express brain-specific nucleic acid and polypeptides.

In eukaryotes, transcription factors have a limited, if not totally cell-type specific, distribution. In addition, each transcription factor typically binds a regulatory element having a very specific nucleic acid sequence. Transcription factors also can function in conjunction with other transcription factors such that the binding to a particular regulatory element is influenced. Thus, the presence of these regulatory elements provides a means for regulating gene expression. Generally, regulatory elements located near transcriptional start sites are known as promoters whereas those located at greater distances from transcriptional start sites are known as enhancers. Further, promoters are typically upstream of the transcriptional start site and only function in one orientation. For example, inverting a promoter sequence usually results in a dramatic decrease in the expression of a downstream gene. Enhancers, however, can be upstream, downstream, or within the nearby gene and can often function in both orientations. For example, an enhancer sequence can be within an intron of the gene it controls.

Many polypeptides and nucleic acids have specific and unique expression patterns. For example, an early polypeptide marker for most, but not all, stem cells in the central nervous system (CNS) is nestin, an intermediate filament polypeptide (Dahlstrand et al., 1995; Frederiksen and McKay, 1988; Hockfield S and R D G McKay, *J. Neurosci.* 5:3310–3328 (1985); Lendahl et al., 1990; Reynolds B A and S Weiss, *Science* 255:1707–1710 (1992);Williams B P and J Price, *Neuron* 14:1–20 (1995)). Upon neuronal differentiation, a switch in intermediate filament gene expression replaces nestin with the neurofilaments (Lendahl U et al., *Cell* 60:585–95 (1990)); reviewed in Lee M K and D W Cleveland., *Annu. Rev. Neurosci.* 19:187–217 (1996)). In the adult CNS, nestin is re-expressed in reactive astrocytes (Clarke et al., 1995; Frisén J et al., *J. Cell Biol.* 131:453–464 (1995)) and in CNS neuroepithelial tumors, most notably gliomas and glioblastomas (Dahlstrand J et al., *Cancer Res.* 52:5334–5341 (1992) and Tohyama T et al., *Lab. Invest.* 66:303–313 (1992)). During embryonic development, nestin expression is not restricted to the CNS. Nestin is also found in myogenic precursors (Kachinsky A M et al., *Dev. Biol.* 165:216–228 (1994); Lendahl U et al., *Cell* 60:585–595 (1990); Sejersen T and U Lendahl, *J. Cell Sci.* 106:1291–1300 (1993)), the peripheral nervous system (Dahlstrand J, et al., *Dev. Brain Res.* 84:109–129 (1995); Hockfield S and RDG McKay, *J. Neurosci.* 5:3310–3328 (1985); and Stemple D L and D J Anderson, *Cell* 71:973–985 (1992)), the heart (Kachinsky A M et al., *J. Histochem. Cytochem.* 43:843–847 (1995)), the developing tooth bud (Terling C et al., *Int. J. Dev. Biol.* 39:947–956 (1995)) and the testis (Fröjdman K et al., Differentiation 61:243–249 (1997)).

Recently, the regulation of nestin gene expression during development was studied using transgenic mice (Zimmerman L B et al., *Neuron* 12:11–24 (1994)). Interestingly, the upstream promoter region of the gene does not possess any enhancer elements specific for neural stem cells. Instead, two separate enhancer regulatory elements were identified within the rat nestin gene: a myogenic precursor cell-specific enhancer within the first intron and a CNS cell-specific enhancer within the second intron. These results demonstrate the presence of multiple regulatory elements within a single gene that each control its expression in distinct tissues.

Tissue-specific regulatory elements are powerful tools that can direct heterologous nucleic acid and polypeptide expression. Indeed, the second intron from the nestin gene directs heterologous gene expression to the developing nervous system (Lardelli M et al., *Mech. Dev.* 59:177–190 (1996); Ringstedt T et al., *Developnzent* 124:2603–2613 (1997); and Lothian C and U Lendahl, *Eur. J. Neurosci.* 9:452–462 (1997)). Most, if not all, gene therapy approaches benefit from tissue-specific regulatory elements since these elements direct expression of the nucleic acid and/or polypeptide of interest to specific target tissues.

SUMMARY

The present invention relates to tissue-specific nucleic acid expression. Specifically, this invention relates to the discovery of regulatory elements that direct the expression of nucleic acid in a tissue-specific manner. The invention provides midbrain-specific and nervous system (NS)-specific regulatory elements as well as elements that potentiate nucleic acid expression and cooperate with other regulatory elements. In addition, the invention provides regulatory elements that direct the expression of nucleic acid in a temporally regulated manner. These elements are particularly useful for gene therapy approaches that require expression in only a specific cell population or at only particular times. The invention also provides nucleic acid constructs that contain these regulatory elements in combination with selected nucleic acid sequences. In addition, the invention provides cells and animals that contain these regulatory elements and constructs as well as methods of providing an animal with a selected nucleic acid sequence that is expressed in a tissue-specific or temporal manner.

One aspect of the invention provides an isolated midbrain-specific regulatory element. An isolated midbrain-specific regulatory element can be isolated from a nestin gene and can contain the nucleic acid sequence of SEQ ID NO:1.

Another aspect of the invention provides an isolated potentiating regulatory element. Isolated potentiating regulatory elements can contain the nucleic acid sequence of SEQ ID NO:2.

Another aspect of the invention provides an isolated nervous system-specific regulatory element that is less than about 400 bases. In addition, an isolated nervous system-specific regulatory element can be less than about 200 bases or less than about 100 bases. Isolated nervous system-specific regulatory elements can contain the nucleic acid sequence of SEQ ID NO:3.

Another aspect of the invention provides an isolated cooperating regulatory element. Isolated cooperating regulatory elements can contain the nucleic acid sequence of SEQ ID NO:4.

Another aspect of the invention provides an isolated temporal midbrain-specific regulatory element. Isolated temporal midbrain-specific regulatory elements can contain the nucleic acid sequence of SEQ ID NO:5.

Another aspect of the invention provides a nucleic acid construct containing an isolated midbrain-specific regulatory element and a selected nucleic acid sequence. A selected nucleic acid sequence can encode a polypeptide. In addition, these constructs can contain an isolated potentiating regulatory element. Further, the invention provides prokaryotic (e.g. *E. coli*) and eukaryotic (e.g., mammalian) cells as well as animals that contain these nucleic acid constructs.

Another aspect of the invention provides a nucleic acid construct containing an isolated potentiating regulatory element and a selected nucleic acid sequence. Again, a selected nucleic acid sequence can encode a polypeptide. Further, the invention provides prokaryotic (e.g. *E. coli*) and eukaryotic (e.g., mammalian) cells as well as animals that contain these nucleic acid constructs.

Another aspect of the invention provides a nucleic acid construct containing two portions. The first portion contains an isolated nervous system-specific regulatory element and is less than about 400 bases. The second portion contains a selected nucleic acid sequence. Again, a selected nucleic acid sequence can encode a polypeptide. In addition, these constructs can contain a third portion. This third portion can contain an isolated cooperating regulatory element and/or an isolated potentiating regulatory element. Further, the invention provides prokaryotic (e.g. *E. coli*) and eukaryotic (e.g., mammalian) cells as well as animals that contain these nucleic acid constructs.

Another aspect of the invention provides a nucleic acid construct containing an isolated cooperating regulatory element and a selected nucleic acid sequence. Again, a selected nucleic acid sequence can encode a polypeptide. Further, the invention provides prokaryotic (e.g. *E. coli*) and eukaryotic (e.g., mammalian) cells as well as animals that contain these nucleic acid constructs.

Another aspect of the invention provides a nucleic acid construct containing an isolated temporal midbrain-specific regulatory element and a selected nucleic acid sequence. Again, a selected nucleic acid sequence can encode a polypeptide. Further, the invention provides prokaryotic (e.g. *E. coli*) and eukaryotic (e.g., mammalian) cells as well as animals that contain these nucleic acid constructs.

Another aspect of the invention provides a method of providing an animal (e.g., mammal) with a selected nucleic acid sequence that is expressed in a tissue-specific manner. The method involves administering a nucleic acid construct containing an isolated midbrain-specific regulatory element and a selected nucleic acid sequence to the animal. Alternatively, the method involves administering a nucleic acid construct containing two portions to the animal. The first portion containing an isolated nervous system-specific regulatory element and being less than about 400 bases. The second portion containing a selected nucleic acid sequence. Again, a selected nucleic acid sequence can encode a polypeptide.

Another aspect of the invention provides a method of providing an animal (e.g., mammal) with a selected nucleic acid sequence that is expressed in a temporal manner. The method involves administering a nucleic acid construct containing an isolated temporal midbrain-specific regulatory element and a selected nucleic acid sequence to the animal.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims,

DESCRIPTION OF DRAWINGS

FIG. 1 is a diagram depicting various constructs and the corresponding LacZ expression results.

FIG. 2 is a series of photographs depicting β-galactosidase activity in whole mount transgenic embryos (10.5 dpc). Representative transgenic embryos are depicted as follows: A, Construct 1; B, Construct 4; C, Construct 5; D, Construct 8; E, Construct 10; F, Construct 11; G, Construct 15; H, Construct 19; and I, Construct 20.

DETAILED DESCRIPTION

Figure 3L:
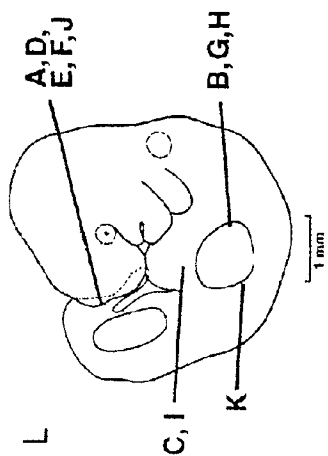
FIG. 3 is a series of photographs depicting the cellular localization of regulatory element activity and the endogenous nestin polypeptide immunoreactivity. Histologic cross and transverse sections were obtained from either LacZ-stained transgenic embryos (Panels A–I) or from normal control embryos (Panels J–K) at a thickness of 10 μm. A schematic of a 10.5 dpc embryo depicting the sectioning planes is presented in Panel L. Various regions are indicated as follows: m, midbrain; h, hindbrain; n, notochord; and fp, floor plate. Dorsal is to the right. Representative transgenic embryos and normal controls are depicted as follows: A–C, Construct 1; D, Construct 4; E, Construct 8; F–G, Construct 19; H–I, Construct 20; and J–K, immunohistochemistry for nestin. Midbrain cells are indicated with a white arrow (Panels A, D–F, and J) and post-mitotic regions of the ventral horns where presumptive motor neurons are differentiating are indicated with a black arrow (Panel K).

The invention provides methods and materials related to tissue-specific nucleic acid expression. Specifically, the invention provides midbrain-specific and NS-specific regulatory elements as well as regulatory elements that potentiate nucleic acid expression and regulatory elements that cooperate with other regulatory elements. In addition, the invention provides temporal regulatory elements that regulate nucleic acid expression in a temporal manner. Further, the invention provides nucleic acid constructs that contain these regulatory elements in combination with selected nucleic acid sequences. The invention also provides cells and animals that contain these regulatory elements and constructs as well as methods of providing an animal with a selected nucleic acid sequence that is expressed in a tissue-specific or temporal manner.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand.

Typically, regulatory elements are DNA sequences that regulate the expression of other DNA sequences at the level of transcription. Thus, regulatory elements include, without limitation, promoters, enhancers, and the like. In addition, regulatory elements can be, without limitation, synthetic DNA, genomic DNA, intron DNA, exon DNA, and naturally-occurring DNA as well as non-naturally-occurring DNA. It is noted that isolated regulatory elements are not required to be DNA even though regulatory elements are typically DNA sequences. For example, regulatory elements can be RNA or RNA/DNA hybrids provided they contain or produce a transcriptionally active regulatory element. Thus, recombinant retroviruses having an RNA sequence that contains an active regulatory element or that produces a regulatory element upon synthesis into DNA by reverse transcriptase are viruses having an isolated regulatory element even though the recombinant retroviruses do not contain any DNA.

The term "isolated" as used herein with reference to nucleic acid such as a regulatory element refers to a naturally-occurring nucleic acid sequence that is not immediately contiguous with both of the sequences with which it is immediately contiguous (one on the 5' end and one on the 3' end) in the naturally-occurring genome of the organism from which it is derived. For example, an isolated nucleic acid molecule can be, without limitation, a recombinant DNA molecule of any length, provided one of the nucleic acid sequences normally found immediately flanking that recombinant DNA molecule in a naturally-occurring genome is removed or absent. Thus, an isolated nucleic acid molecule includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" also includes any non-naturally-occurring nucleic acid sequence since non-naturally-occurring nucleic acid sequences are not found in nature and do not have immediately contiguous sequences in a naturally-occurring genome. For example, non-naturally-occurring nucleic acid sequences such as engineered nucleic acid sequences are isolated nucleic acid sequences. Engineered nucleic acid sequences can be made using common molecular cloning or chemical nucleic acid synthesis techniques. Isolated non-naturally-occurring nucleic acid sequences can be independent of other sequences or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid sequence can include a nucleic acid molecule that is part of a hybrid or fusion nucleic acid sequence.

Although this invention is not limited to any specific mode of action, regulatory elements provide sequence-specific binding sites for nucleic acid binding polypeptides including, but not limited to, transcription factors, and it is presumably the binding of a nucleic acid binding polypeptides to a regulatory element that regulates the transcription of another nucleic acid sequence. The regulatory element and the nucleic acid sequence regulated by the regulatory element must be located on the same nucleic acid molecule for regulated expression to occur. The distance, however, between the regulatory element and the regulated sequence can be any distance, provided regulation occurs. For example, a regulatory element, such as a promoter, can be a few bases upstream of a sequence to be regulated or a regulatory element, such as an enhancer, can be a few hundred kilobases upstream or downstream of a sequence to be regulated. In both cases, the regulatory element and the regulated sequence are considered nearby. Thus, the term "nearby" as used herein includes distances from a few bases to hundreds of kilobases provided that the functional relationship between the regulatory element and the regulated sequence remains intact. Further, regulatory elements can be in any orientation with respect to the nearby nucleic acid sequence. For example, a regulatory element can be 5'-XXXYYY-3' or inverted to read 5'-YYYXXX-3'. In addition, nucleic acid binding polypeptides can function in conjunction with other nucleic acid binding polypeptides such that the binding to a particular regulatory element is influenced.

A tissue-specific regulatory element is any regulatory element that confers a tissue-specific expression pattern to a nearby nucleic acid sequence. In general, any regulatory element that confers expression non-specifically (e.g., random expression throughout an organism having no consistent or recognizable pattern) is not a tissue-specific regulatory element. In addition, any regulatory element that is a ubiquitous regulatory element is not a tissue-specific regulatory element. Thus, at least at a given time point, tissue-specific regulatory elements are elements that confer the expression of a nearby nucleic acid sequence to a limited set of cells in an organism and not to a random array of cells or to every cell in that organism. This limited set of cells can be cells from a single organ such as liver, cells of a particular type such as lymphocytes, or cells at a particular stage in development such as progenitor cells. In addition, the limited set of cells defining the tissue-specificity can include multiple seemingly diverse cell populations such as skin cells and neurons. Each of the seemingly diverse cells expressing the nearby nucleic acid sequence presumably contain a similar set of transcription factors that bind to the regulatory element(s) and facilitate transcription of the nearby sequence. Again, the invention is not limited to any specific mode of action.

It is noted that tissue-specific regulatory elements confer tissue-specific expression and do not necessarily drive tissue-specific expression by themselves. In other words, a tissue-specific regulatory element, by itself (i.e., the regulatory element and the nearby nucleic acid sequence only), may not drive any expression of a nearby nucleic acid sequence. A tissue-specific regulatory element, however, confers tissue-specific expression on a nearby nucleic acid sequence, for example, in conjunction with another regulatory element such as a non-tissue-specific regulatory element.

Midbrain-specific Regulatory Elements

A midbrain-specific regulatory element is any regulatory element that confers a midbrain-specific expression pattern to a nearby nucleic acid sequence. The term "midbrain-specific expression pattern" is defined in relation to the entire CNS, or developing CNS, and means that a nearby nucleic acid sequence is expressed by midbrain cells. Midbrain cells include, without limitation, midbrain progenitor cells of the mesencephalon as well as any cell derived from midbrain progenitor cells of the mesencephalon, such as post-mitotic midbrain neurons and glia of the superior colliculus, inferior colliculus, periaquaductal gray, red nucleus, and substantia nigra and. A midbrain-specific expression pattern also means that few, if any, cells other than midbrain cells express the nearby nucleic acid sequence. Cells other than midbrain cells include, without limitation, non-midbrain cells in the CNS such as neurons and glia of the hypothalamus and cortex as well as non-midbrain progenitor cells in the developing nervous system such as neuroepithelial cells of the diencephalon, telencephalon, and spinal cord. Midbrain-specific regulatory elements can be, for example, mammalian midbrain-specific regulatory elements. A mammalian midbrain-specific regulatory element is any midbrain-specific regulatory element that contains a sequence based upon a sequence from a mammalian genome.

In addition, a midbrain-specific regulatory element can confer a midbrain-specific expression pattern constitutively or transiently. In other words, a midbrain-specific regulatory element can confer a midbrain-specific expression pattern either continuously or for a limited time period during an animal's lifetime. In this context, the term "lifetime" includes any time from fertilization to death. Thus, a midbrain-specific regulatory element can confer, for example, expression of a nucleic acid sequence to the midbrain tegmentum region during development and not confer expression to midbrain cells during adulthood. Thus, midbrain-specific regulatory elements are not restricted to a particular time period for expression, provided the midbrain regulatory element confers midbrain-specific expression at, at least, some time during an animal's lifetime.

The term "stem cell" refers to an unspecialized cell that gives rise to differentiated cells. Thus, a neuronal stem cell is an unspecialized neuronal cell that can give rise to a specialized neuron such as a dopaminergic neuron of the substantia nigra. For the purpose of this invention, all neuroepithelial cells of the mesencephalon are considered to be midbrain stem cells. Likewise, all neuroepithelial cells of the diencephalon, telencephalon, mesencephalon, myelencephalon, and metencephalon are considered to be NS stem cells. The term "nervous system" includes both the central nervous system and peripheral nervous system (PNS). During early embryogenesis, when the PNS has not yet begun to develop, the term "CNS" may be used instead of "NS" to refer to the entire nervous as it exists at that point in time.

A midbrain-specific regulatory element can be, without limitation, a nucleic acid sequence identical to or similar to the nucleic acid sequence described in SEQ ID NO:1, provided the nucleic acid sequence functions as a midbrain-specific regulatory element. SEQ ID NO:1 has the following nucleic acid sequence: 5'-ACTAGTTCCG AATCCCATGT GAACTGATTT CCCTCATCTC CTTCAATCAG CTCCATAGGC CACTGAGGCA GGGCCATGAA CGTTAAGACC TCTGCCCTGA AGAGTTTGTG ATCCTGAGAT GAGGGCTTTA GC-3'.

Sequences identical to or similar to the sequence described in SEQ ID NO:1 can be identified, for example, by computer programs designed to perform single and multiple sequence alignments. In addition, identical and similar sequences can be identified by standard hybridization techniques. For example, nucleic acid sequences having at least about 70% sequence identity to the sequence of SEQ ID NO:1 are within the scope of the invention and can be identified by hybridization under conditions of moderate stringency. Further, nucleic acid sequences having at least about 80%, 90%, or 95% sequence identity to the sequence of SEQ ID NO:1 can be identified by high stringency hybridization. Thus, similar nucleic acid sequences can include nucleic acid sequences that are about 70%, 80%, 90%, 95%, 98%, or 99% identical to the sequence described in SEQ ID NO:1. It follows that similar nucleic acid sequences can be identified as any sequence that hybridizes with the sequence described in SEQ ID NO:1 under moderate to high stringency conditions.

High stringency conditions are used to identify nucleic acid sequences that have a high degree of homology or sequence identity to a probe. High stringency conditions can include the use of a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% fornamide, 5×SSC (0.75 M NaCl, 0.075 M sodium citrate), 50 mM sodium phosphate (pH 6.5), 0.1% sodium pyrophosphate, 5×Denhardt's solution, sonicated salmon sperm DNA (50 ug/ml), 0.1% sodium lauryl sulfate (SDS), and 10% dextan sulfate at 42° C., with washes at 42° C. in 0.2×SSC and 0.1% SDS. Alternatively, low ionic strength and high temperature can be used for washing, for example, 0.1×SSC (0.015 M NaCl/0.0015 M sodium citrate), 0.1% SDS at 65° C.

Moderate stringency conditions are hybridization conditions used to identify nucleic acid sequences that have less homology or identity to a probe than do nucleic acid sequences identified under high stringency conditions. Moderate stringency conditions can include the use of higher ionic strength and/or lower temperatures for washing of the hybridization membrane, compared to the ionic strength and temperatures used for high stringency hybridization. For example, a wash solution of 4×SSC (0.06 M NaCl/0.006 M sodium citrate), 0.1% SDS can be used at 50° C., with a last wash in 1×SSC at 65° C. Alternatively, a hybridization wash in 1×SSC at 37° C. can be used.

Hybridization can be done by Southern or Northern analysis to identify a DNA or RNA sequence, respectively, that hybridizes to a probe. The probe can be labeled with a radioisotope such as $^{32}$p, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence within SEQ ID NO:1 can be used to identify a nucleic acid sequence identical to or similar to the nucleic acid sequence of SEQ ID NO:1. In addition, probes longer or shorter than 20 nucleotides can be used.

In addition, a midbrain-specific regulatory element can be a nucleic acid sequence having a variation of a sequence identical to or similar to the sequence described in SEQ ID NO:1, provided this sequence can function as a midbrain-specific regulatory element. Variations to such sequences can include, without limitation, deletions, insertions, and base substitutions, as well as combinations of deletions, insertions, and base substitutions. Thus, nucleic acid sequences longer and shorter than the sequence described in SEQ ID NO:1 that function as midbrain-specific regulatory elements are within the scope to the invention. For example, sequences that contain a stretch of about four to eight nucleotides that are identical to a stretch found in SEQ ID NO:1 are considered variations of SEQ ID NO:1 and are midbrain-specific regulatory elements provided they function as midbrain-specific regulatory elements. Likewise, nucleic acid sequences having about 61% sequence identity to the sequence described in SEQ ID NO:1 are midbrain-specific regulatory elements provided they function as midbrain-specific regulatory elements. It is noted that, depending on the degree of homology, sequences that are variants of SEQ ID NO:1 can also be similar to SEQ ID NO:1 as defined by, for example, the hybridization conditions above.

Further, a midbrain-specific regulatory element can be any nucleic acid sequence, provided this sequence can function as a midbrain-specific regulatory element. Thus, nucleic acid sequences that function as midbrain-specific regulatory elements and do not contain any sequence homology to the sequence described in SEQ ID NO:1 are considered midbrain-specific regulatory elements within the scope of the invention.

Midbrain-specific regulatory elements lacking homology with SEQ ID NO:1, as well as those that are homologous, can be obtained by chemical synthesis, isolation and cloning from genomic DNA, or other means known in the art, including the use of PCR technology carried out using, for example, oligonucleotides corresponding to portions of SEQ ID NO:1. Alternatively, a midbrain-specific regulatory element can by obtained using an enhancer trap assay. An enhancer trap assay involves introducing a reporter, or any other detectable nucleic acid sequence, into the genome in the vicinity of an endogenous regulatory element. The activation of the reporter indicates the existence of a regulatory element that can be subsequently isolated. This approach can be used with cell lines, transgenic mice, and embryonic stem cells in culture or in vivo (Gossler et al., *Science* 244:463–465 (1989)). In addition, the introduced reporter can be modified to specifically enrich for regulatory elements by a variety of methods known in the art (Gossler and Zachgo, In: Gene targeting: a practical approach. ed. A L Joyner, IRL Press, Oxford, NY, Tokyo (1993)).

PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. PCR can be used to amplify a nucleic acid sequence from RNA or DNA. For example, a nucleic acid sequence can be isolated by PCR amplification from total cellular RNA, total genomic DNA, and cDNA transcribed from RNA, as well as from bacteriophage sequences, plasmid sequences, viral sequences, and the like. When using RNA as a source of template, reverse transcriptase needs to be used to synthesize complimentary DNA strands.

The following methods can be used to identify nucleic acid sequences that function as midbrain-specific regulatory elements. These nucleic acid sequences can be, as described above, identical or similar to SEQ ID NO:1, a variation of SEQ ID NO:1, or non-homologous to SEQ ID NO:1. Generally, a construct is made to contain a given nucleic acid sequence to be tested for midbrain-specific regulatory element function and at least one nearby reporter or marker sequence that can be monitored for expression. This construct is introduced into both midbrain and non-midbrain cells and the expression of the reporter or marker in each cell type is determined and compared. If midbrain cells express the reporter or marker and most, if not all, non-midbrain cells do not, then the given nucleic acid sequence is a midbrain-specific regulatory element within the scope of the invention.

For the purpose of this invention, any sequence can be a reporter or marker provided its expression can be detected at either the RNA or polypeptide level. Reporter and/or marker sequences can include, without limitation, sequences that encode β-lactamase, chloramphenicol acetyltransferase (CAT), adenosine deaminase (ADA), aminoglycoside phosphotransferase (neor, G418′), dihydrofolate reductase (DHFR), hygromycin-B-phosphotransferase (HPH), thymidine kinase (TK), β-galactosidase, xanthine guanine phosphoriboxyltransferase (XGPRT), green fluorescent protein (GFP), GFP variants, SV40 large T antigen, alkiline phosphatase, growth hormones, and the like. The expression of the reporter or marker sequence in cells can be determined in vivo, ex vivo, in vitro, and in situ using methods known in the art. For example, the expression of LacZ (encoding β-galactosidase) can be assayed using intact embryos or tissue sections containing midbrain and non-midbrain cells derived from an embryo or organism. In addition, the midbrain and non-midbrain cells can be in vivo or in vitro. Thus, a construct can be introduced into an organism containing midbrain and non-midbrain cells or into midbrain and non-midbrain cells in culture. For example, a construct can be introduced into primary cultures of midbrain and non-midbrain cells and assayed for reporter sequence expression. When using culture systems, it is important to determine that the cultured cells are in fact midbrain cells or appropriate equivalents thereof. This can be accomplished by comparing the polypeptides expressed by genuine midbrain cells found in vivo with those expressed by the particular cultured cells.

The constructs used to identify midbrain-specific regulatory elements can contain additional regulatory elements that do not interfere with the identification of midbrain-specific regulatory element activity. These additional regulatory elements can be, without limitation, promoters, enhancers, and the like. In addition, these additional regulatory elements typically aid or facilitate the identification of midbrain-specific regulatory elements. For example, a construct containing a given nucleic acid sequence to be tested for midbrain-specific regulatory element function can also contain a minimal promoter sequence, such as a portion of an upstream sequence from the herpes simplex virus ICP4 gene, the TK gene, or a heat shock gene. In this case, the minimal promoter sequence can help drive the expression of the reporter sequence in midbrain cells only when a midbrain-specific regulatory element is present. Thus, the minimal promoter would not necessary drive expression in non-midbrain cells or in midbrain cells in a predictable or consistent manner when the midbrain-specific regulatory element is not present.

Methods and techniques for delivering or administering nucleic acid to cells, whether in vivo or in vitro, are well known to those skilled in the art. For example, calcium phosphate precipitation, electroporation, heat shock, lipofection, microinjection, and viral-mediated nucleic acid transfer are common methods of introducing nucleic acid into cells. In addition, naked DNA can be delivered directly to cells in vivo as describe elsewhere (U.S. Pat. No. 5,580,859 and U.S. Pat. No. 5,589,466 including continuations thereof). Further, nucleic acid can be introduced into cells by generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce nucleic acid into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA*, 82:6148 (1985)); gene transfection into embryonic stem cells (Gossler A et al., *Proc Natl Acad Sci USA* 83:9065–9069 (1986)); gene targeting into embryonic stem cells (Thompson et al., *Cell*, 56:313 (1989)); nuclear transfer of somatic nuclei (Schnieke A E et al., *Science* 278:2130–2133 (1997)); and electroporation of embryos (Lo, *Mol. Cell. Biol*., 3:1803 (1983)).

For a review of techniques that can be used to generate and assess transgenic animals, skilled artisans can consult Gordon (*Intl. Rev. Cytol*., 115:171–229 (1989)), and may obtain dditional guidance from, for example: Hogan et al., "Manipulating the Mouse Embryo" Cold Spring Harbor Press, Cold Spring Harbor, N.Y. (1986); Krimpenfort et al., *Bio/Technology*, 9:86 (1991); Palmiter et al., *Cell*, 41:343 (1985); Kraemer et al., "Genetic Manipulation of the Early Mammalian Embryo" Cold Spring Harbor Press, Cold Spring Harbor, N.Y. (1985); Hammer et al., *Nature*, 315:680 (1985); Purcel et al., *Science*, 244:1281 (1986); Wagner et al., U.S. Pat. No. 5,175,385; and Krimpenfort et al., U.S. Pat. No. 5,175,384.

Typically, a construct containing a given nucleic acid sequence to be tested for midbrain-specific regulatory element function, a minimal promoter sequence such as a portion of an upstream sequence from the herpes simplex virus ICP4 gene, and a reporter sequence such as the LacZ sequence is used to generate transgenic embryos. For example, a plasmid containing the construct can be treated with restriction endonucleases to generate a DNA fragment that contains the construct. The fragment corresponding to the construct can be isolated by agarose gel electrophoresis and purified over Qiagen columns or any other method. The purified DNA can be diluted to a final concentration of 2.0 μg/ml in a TE buffer (10 mM Tris-C1 pH 7.3; 0.25 mM EDTA) for microinjection. FVB mice or any other mouse strains and combinations can be used as donors for microinjection and CD-1 mice can be used as foster mothers following standard protocols of Hogan B et al. (Cold Spring Harbor, N.Y.: Cold Spring Harbor Laboratory Press) (1994). To identify transgenic embryos, genomic DNA can be isolated from the yolk sac of each embryo and tested for the presence of the LacZ transgene by southern hybridization or PCR using primers specific for the LacZ sequence such as 5'-GACGGGTTGTTACTCGCTCAC-3' (SEQ ID NO:7) and 5'-GCGTGTACCACAGCGGATGGT-3' (SEQ ID NO:8). These primers will amplify a 868 bp product corresponding to the LacZ transgene. PCR conditions can be as follows: an initial denaturation step at 94° C. for 5 minutes; 35 cycles at 94° C. for 30 seconds, 62° C. for 1 minute, and 72° C. for 30 seconds; and a final extension step at 72° C. for 5 minutes.

Transgenic embryos can be isolated and examined for β-galactosidase activity at various developmental stages such as 10.5 days post coitum (dpc) with the morning of the microinjection designated as 0.5 dpc. Embryos can be fixed in 4% paraformaldehyde in PBS at 4° C. for 2 hours at 10.5 dpc and for 3 hours at 13.5 dpc. The fixative can be removed with three 15 minute washes at 37° C. in a buffer of 100 mM $NaH_2PO_4$(pH 7.3), 2 mM $MgCl_2$, 0.1% deoxycholate, 0.2% NP-40. Staining can proceed in the same buffer supplemented with 5 mM $K_3Fe(CN)_6 \cdot 3H_2O$, 5 mM $K_4Fe(CN)_6$, and 1 mg/ml X-gal. Staining is monitored after 1 hour and allowed to proceed overnight. The reaction can be stopped by rinsing with PBS and post-fixing the embryos in 4% paraformaldehyde/0.25% glutaraldehyde in PBS for 4 hours at 4° C. Embryos can be dehydrated in 70% ethanol and photographed on a Leica Stereo Zoom M3Z microscope. In addition, histologic sections can be obtained by embedding the embryos in paraffin wax followed by microtome sectioning at 10 μm thickness. These sections can be analyzed and photographed with a Leica DMRB microscope.

The expression of the LacZ sequence by midbrain cells can be determined by the visualization of blue staining in whole mount embryos and histologic sections. Negative controls can include, without limitation, non-transgenic embryos as well as transgenic embryos containing a construct that has a non-midbrain-specific regulatory element. Positive controls can include, without limitation, transgenic embryos containing a construct that has the midbrain-specific regulatory element having the nucleic acid sequence of SEQ ID NO:1.

If LacZ is determined to be expressed by midbrain cells and few, if any, cells other than midbrain cells, then the given nucleic acid sequence is a midbrain-specific regulatory element within the scope of the invention.

Potentiating Regulatory Elements

A potentiating regulatory element is any regulatory element that functions in conjunction with a tissue-specific regulatory element to increase the frequency at which a nearby nucleic acid sequence is expressed such that the tissue specificity of the tissue-specific regulatory element is maintained. Potentiating regulatory elements do not confer tissue-specific expression on the nearby nucleic acid sequence, but rather they increase the frequency of expression conferred by another tissue-specific regulatory element such that the original tissue-specificity of the other regulatory element is maintained. This other regulatory element is referred to as a potentiated regulatory element. Thus, the term "increases the frequency" is defined in relation to a potentiated regulatory element, and means that a nearby nucleic acid sequence is expressed more often than if the potentiating regulatory element were deleted or otherwise rendered inactive. For example, more transgenic animals containing a construct that contains a potentiating regulatory element can express a nearby nucleic acid sequence than transgenic animals containing the identical construct lacking the potentiating regulatory element.

In addition, a potentiating regulatory element is any regulatory element that increases the number of cells expressing a nearby nucleic acid sequence provided the original tissue specificity of the potentiated regulatory element is maintained. For example, transgenic animals containing a construct that contains a midbrain-specific regulatory element (potentiated regulatory element) and a potentiating regulatory element can express a nearby nucleic acid sequence in more midbrain cells than transgenic animals containing the identical construct lacking the potentiating regulatory element. In this case, both sets of transgenic animals exhibit a tissue-specific (e.g., midbrain-specific) expression pattern.

Further, a potentiating regulatory element is any regulatory element that increases the level of expression of a nearby nucleic acid sequence provided the original tissue specificity of the potentiated regulatory element is maintained. For example, transgenic animals containing a construct that contains midbrain-specific regulatory element and a potentiating regulatory element (potentiated regulatory element) can express a nearby nucleic acid sequence at a higher level in midbrain cells than transgenic animals containing the identical construct lacking the potentiating regulatory element. In this case, both sets of transgenic animals exhibit an identical tissue expression pattern with only the level of express varying.

It is noted that potentiating regulatory elements by themselves may not direct the expression of any nearby nucleic acid sequence. Potentiating regulatory elements, however, can function with other regulatory elements to direct nucleic acid expression. Examples of other regulatory elements that can have their activity potentiated by a potentiating regulatory element include, without limitation, tissue-specific promoters and enhancers such as the tyrosine hydroxylase promoter, midbrain-specific regulatory element, NS-specific regulatory element, and neurofilament promoter. In addition, potentiating regulatory elements can be, for example, mammalian potentiating regulatory elements. A mammalian potentiating regulatory element is any potentiating regulatory element that contains a sequence based upon a sequence from a mammalian genome.

Potentiating regulatory elements can potentiate expression constitutively or transiently. In other words, a potentiating regulatory element can increase the frequency of expression either continuously or for a limited time period during an animal's lifetime. Thus, potentiating regulatory elements are not restricted to a particular time period, provided the potentiating regulatory element increase the frequency of expression at, at least, some time during an animal's lifetime.

A potentiating regulatory element can be, without limitation, a nucleic acid sequence identical to or similar to the nucleic acid sequence described in SEQ ID NO:2, provided the nucleic acid sequence functions as a potentiating regulatory element. SEQ ID NO:2 has the following nucleic acid sequence: 5'-CCCAGTCAGT CCTCTGAGGG GAAGGGTCCA GGCAGCTCTG AGGAATGTA ACCACTG-3'.

Sequences identical to or similar to the sequence described in SEQ ID NO:2 can be identified by sequence alignments and standard hybridization techniques described herein. For example, nucleic acid sequences having at least about 70% sequence identity to the sequence of SEQ ID NO:2 are within the scope of the invention and can be identified by hybridization under conditions of moderate stringency. Further, nucleic acid sequences having at least about 80%, 90%, or 95% sequence identity to the sequence of SEQ ID NO:2 can be identified by high stringency hybridization. Thus, similar nucleic acid sequences can include nucleic acid sequences that are about 70%, 80%, 90%, 95%, 98%, or 99% identical to the sequence described in SEQ ID NO:2. It follows that similar nucleic acid sequences can be identified as any sequence that hybridizes with the sequence described in SEQ ID NO:2 under moderate to high stringency conditions.

In addition, a potentiating regulatory element can be a nucleic acid sequence having a variation of a sequence identical to or similar to the sequence described in SEQ ID NO:2, provided this sequence can function as a potentiating regulatory element. Variations to such sequences can include, without limitation, deletions, insertions, and base substitutions, as well as combinations of deletions, insertions, and base substitutions. Thus, nucleic acid sequences longer and shorter than the sequence described in SEQ ID NO:2 that function as potentiating regulatory elements are within the scope to the invention. For example, sequences that contain a stretch of about four to eight nucleotides that are identical to a stretch found in SEQ ID NO:2 are considered variations of SEQ ID NO:2 and are potentiating regulatory elements provided they function as potentiating regulatory elements. It is noted that, depending on the degree of homology, sequences that are variants of SEQ ID NO:2 can also be similar to SEQ ID NO:2 as defined by, for example, the hybridization conditions above.

Further, a potentiating regulatory element can be any nucleic acid sequence, provided this sequence can function as a potentiating regulatory element. Thus, nucleic acid sequences that function as potentiating regulatory elements and do not contain any sequence homology to the sequence described in SEQ ID NO:2 are considered potentiating regulatory elements within the scope of the invention.

Potentiating regulatory elements lacking homology with SEQ ID NO:2, as well as those that are homologous, can be obtained by chemical synthesis, isolation and cloning from genomic DNA, or other means known in the art, including the use of trap assays and PCR technology carried out using, for example, oligonucleotides corresponding to portions of SEQ ID NO:2.

The following methods can be used to identify nucleic acid sequences that function as potentiating regulatory elements. These nucleic acid sequences can be, as described above, identical or similar to SEQ ID NO:2, a variation of SEQ ID NO:2, or non-homologous to SEQ ID NO:2. Generally, a construct is made to contain a known regulatory element (potentiated regulatory element), a given nucleic acid sequence to be tested for potentiating regulatory element function, and at least one nearby reporter or marker sequence that can be monitored for expression. This construct is introduced into cells and the frequency of expression, the tissue expression pattern, and the level of expression of the reporter or marker are determined and compared to those determined for a similar construct lacking the given nucleic acid sequence. If the frequency of expression, the tissue expression pattern, and/or the level of expression of the reporter or marker sequence is increased and the original tissue-specificity of the known regulatory element is maintained for the construct containing the given nucleic acid sequence when compared with a similar construct lacking the given nucleic acid sequence, then the given nucleic acid sequence is a potentiating regulatory element within the scope of the invention.

Possible reporter and/or marker sequences and methods for introducing nucleic acid into cells are described herein. The expression of the reporter or marker sequence in cells can be determined in vivo, ex vivo, in vitro, and in situ using methods known in the art. For example, the expression of LacZ can be assayed using intact embryos or tissue sections derived from an embryo or organism. In addition, the cells can be in vivo or in vitro. Thus, a construct can be introduced into cells in an organism or into cells in culture. For example, a construct can be introduced into transformed cell lines or primary cultures, and assayed for reporter sequence expression. The level of expression increased by a potentiating regulatory element can be measured by quantifying methods such as chemiluminescence, CAT assay, enzyme activities, and the like.

The constructs used to identify potentiating regulatory elements can contain additional regulatory elements that do not interfere with the identification of potentiating regulatory element activity. These additional regulatory elements can be, without limitation, promoters, enhancers, and the like. In addition, these additional regulatory elements typically aid in or facilitate the identification of potentiating regulatory elements. For example, a construct containing a given nucleic acid sequence to be tested for potentiating regulatory element function can also contain a minimal promoter sequence, such as a portion of an upstream sequence from the herpes simplex virus ICP4 gene, the TK gene, or a heat shock gene. The additional regulatory element may, by itself, not direct the expression of any nearby nucleic acid sequence.

Typically, a construct containing a known regulatory element such as a midbrain-specific regulatory element (potentiated regulatory element), a given nucleic acid sequence to be tested for potentiating regulatory element function, a minimal promoter sequence such as a portion of an upstream sequence from the herpes simplex virus ICP4 gene, and a reporter sequence such as the LacZ sequence is used to generate transgenic embryos. These transgenic embryos can be made and analyzed as described herein.

The frequency of LacZ expression by cells, the tissue expression pattern of LacZ, and the level of LacZ expression can be determined by comparing results generated from embryos containing a construct having the given nucleic acid sequence to be tested for potentiating regulatory element function with results generated from embryos containing a similar construct lacking the given nucleic acid sequence to be tested for potentiating regulatory element function. A control experiment can include comparing the results generated from transgenic embryos containing a construct that has the potentiating regulatory element having the nucleic acid sequence of SEQ ID NO:2, such as Constructs 7–10 (see Example 2) with results generated from embryos containing a similar construct lacking this potentiating regulatory element, such as Constructs 11–13.

If the frequency of LacZ expression by cells, the tissue expression pattern of LacZ, and/or the level of LacZ expression is determined to be increased by the presence of the given nucleic acid sequence and the tissue specificity of the potentiated regulatory element is maintained, then the given nucleic acid sequence is a potentiating regulatory element within the scope of the invention.

Nervous System-specific Regulatory Elements

A NS-specific regulatory element is any regulatory element that confers a NS-specific expression pattern to a nearby nucleic acid sequence and is less than about 400 bases in length. The term "NS-specific expression pattern" is defined in relation to an entire organism, or developing embryo, and means that a nearby nucleic acid sequence is expressed by NS cells. NS cells include, without limitation, NS stem cells of the diencephalon, telencephalon, mesencephalon, myelencephalon, and metencephalon as well as any cell derived from NS stem cells of the diencephalon, telencephalon, mesencephalon, myelencephalon, and metencephalon, such as glia and postmitotic neurons of the brain, spinal cord, and PNS. Neuroblastoma and gliomas as well as other cancer cells derived from NS stem cells are also considered NS cells. A NS-specific expression pattern also means that few, if any, cells other than NS cells express the nearby nucleic acid sequence. Cells other than NS cells include, without limitation, non-NS cells in an organism such as muscle and immune cells and non-NS stem cells in a developing embryo such as cells of the mesoderm and endoderm. In addition, NS-specific regulatory elements can be, for example, mammalian NS-specific regulatory elements. A mammalian NS-specific regulatory element is any NS-specific regulatory element that contains a sequence based upon a sequence from a mammalian genome.

The NS-specific regulatory element can confer a NS-specific expression pattern constitutively or transiently. In other words, a NS-specific regulatory element can confer a NS-specific expression pattern either continuously or for a limited time period during an animal's lifetime. Thus, a NS-specific regulatory element can confer, for example, expression of a nucleic acid sequence to the diencephalon, telencephalon, mesencephalon, myelencephalon, and metencephalon during development and not confer expression to brain or spinal cord cells during adulthood. Thus, NS-specific regulatory elements are not restricted to a particular time period for expression, provided the NS-specific regulatory element confers NS-specific expression at, at least, some time during an animal's lifetime.

A NS-specific regulatory element can be, without limitation, a nucleic acid sequence identical to or similar to the nucleic acid sequence described in SEQ ID NO:3, provided the nucleic acid sequence functions as a NS-specific regulatory clement and is less than about 400 bases in length. SEQ ID NO:3 has the following nucleic acid sequence: 5'-GCCCTCCAGA TGGTAGTGTG GACAAAAGGC AATAATTAGC ATGAGAATCG GCCTCCCTCC CAGAGGATGA GGTCATC-3'.

Sequences identical to or similar to the sequence described in SEQ ID NO:3 can be identified by sequence alignments and standard hybridization techniques described herein. For example, nucleic acid sequences having at least about 70% sequence identity to the sequence of SEQ ID NO:3 are within the scope of the invention and can be identified by hybridization under conditions of moderate stringency. Further, nucleic acid sequences having at least about 80%, 90%, or 95% sequence identity to the sequence of SEQ ID NO:3 can be identified by high stringency hybridization. Thus, similar nucleic acid sequences can include nucleic acid sequences that are at least about 70%, 80%, 83%, 90%, 95%, 98%, or 99% identical to the sequence described in SEQ ID NO:3. It follows that similar nucleic acid sequences can be identified as any sequence that hybridizes with the sequence described in SEQ ID NO:3 under moderate to high stringency conditions.

In addition, a NS-specific regulatory element can be a nucleic acid sequence having a variation of a sequence identical to or similar to the sequence described in SEQ ID NO:3, provided this sequence can function as a NS-specific regulatory element and is less than about 400 bases in length. Variations to such sequences can include, without limitation, deletions, insertions, and base substitutions, as well as combinations of deletions, insertions, and base substitutions. Thus, nucleic acid sequences longer and shorter than the sequence described in SEQ ID NO:3 that function as NS-specific regulatory elements are within the scope to the invention, provided the sequence is less than about 400 bases. For example, sequences that contain a stretch of about four to eight nucleotides that are identical to a stretch found in SEQ ID NO:3 are considered variations of SEQ ID NO:3 and are NS-specific regulatory elements provided they function as NS-specific regulatory elements. It is noted that, depending on the degree of homology, sequences that are variants of SEQ ID NO:3 can also be similar to SEQ ID NO:3 as defined by, for example, the hybridization conditions above.

Further, a NS-specific regulatory element can be any nucleic acid sequence, provided this sequence can function as a NS-specific regulatory element and is less than about 400 bases in length. Thus, nucleic acid sequences that function as NS-specific regulatory elements and do not contain any sequence homology to the sequence described in SEQ ID NO:3 are considered NS-specific regulatory elements within the scope of the invention.

NS-specific regulatory elements lacking homology with SEQ ID NO:3, as well as those that are homologous, can be obtained by chemical synthesis, isolation and cloning from genomic DNA, or other means known in the art, including the use of enhancer trap assays and PCR technology carried out using, for example, oligonucleotides corresponding to portions of SEQ ID NO:3.

The following methods can be used to identify nucleic acid sequences that function as NS-specific regulatory elements. These nucleic acid sequences can be, as described above, identical or similar to SEQ ID NO:3, a variation of SEQ ID NO:3, or non-homologous to SEQ ID NO:3. Generally, a construct is made to contain a given nucleic acid sequence less than about 400 bases in length to be tested for NS-specific regulatory element function, and at least one nearby reporter or marker sequence that can be monitored for expression. This construct is introduced into both NS and non-NS cells and the expression of the reporter or marker in each cell type is determined and compared. If NS cells express the reporter or marker and non-NS cells do not, then the given nucleic acid sequence is a NS-specific regulatory element within the scope of the invention.

Possible reporter and/or marker sequences and methods for introducing nucleic acid into cells are described herein. The expression of the reporter or marker sequence in cells can be determined in vivo, ex vivo, in vitro, and in situ using methods known in the art. For example, the expression of LacZ can be assayed using intact embryos or tissue sections derived from an embryo or organism. In addition, the cells can be in vivo or in vitro. Thus, a construct can be introduced into cells in an organism or into cells in culture. For example, a construct can be introduced into transformed cell lines or primary cultures, and assayed for reporter sequence expression. When using culture systems, it is important to determine that the cultured cells are in fact NS cells or appropriate equivalents thereof. This can be accomplished by comparing the polypeptides expressed by genuine NS cells found in vivo with those expressed by the particular cultured cells.

The constructs used to identify NS-specific regulatory elements can contain additional regulatory elements that do not interfere with the identification of NS-specific regulatory element activity. These additional regulatory elements can be, without limitation, promoters, enhancers, and the like. In addition, these additional regulatory elements typically aid in or facilitate the identification of NS-specific regulatory elements. For example, a construct containing a given nucleic acid sequence less than about 400 bases in length to be tested for NS-specific regulatory element function can also contain a cooperating regulatory element as described herein and/or a minimal promoter sequence, such as a portion of an upstream sequence from the herpes simplex virus ICP4 gene, the TK gene, or a heat shock gene. This additional regulatory element may, by itself, not direct the expression of any nearby nucleic acid sequence.

Typically, a construct containing a given nucleic acid sequence less than about 400 bases in length to be tested for NS-specific regulatory element function, a minimal promoter sequence such as a portion of an upstream sequence from the herpes simplex virus ICP4 gene, and a reporter sequence such as the LacZ sequence is used to generate transgenic embryos. The construct can also contain a potentiating and/or cooperating regulatory element to aid in or facilitate the identification of a NS-specific expression pattern. Transgenic embryos can be made and analyzed as described herein.

The expression of the LacZ sequence by NS cells can be determined by the visualization of blue staining in whole mount transgenic embryos and histologic sections. Negative controls can include, without limitation, non-transgenic embryos as well as transgenic embryos containing a construct that has a non-NS-specific regulatory element. Positive controls can include, without limitation, transgenic embryos containing a construct that has the NS-specific regulatory element having the nucleic acid sequence of SEQ ID NO:3 in conjunction with a cooperating regulatory element having the nucleic acid sequence of SEQ ID NO:4. In this case, the positive control will contain the nucleic acid sequence of SEQ ID NO:6. SEQ ID NO:6 has the following nucleic acid sequence: 5'-AAGGATTTGG AGAAGGG-GAG CTGAATTCAT TTGCTTTTGT CTGTTACCAG CTCTGGGGGC AGAGAGAGAG CCATCCCCTG GGAACAGCCT GAGAATTCCC ACTTCCCCTG AGGAGCCCTC CCTTCTTAGG CCCTCCAGAT GGTAGTGTGG ACAAAAGGCA ATAATTAGCA TGAGAATCGG CCTCCCTCCC AGAGGATGAG GTCATC-3'.

If LacZ is determined to be expressed by NS cells and few, if any, cells other than NS cells and the given nucleic acid sequence is less than about 400 bases in length, then the given nucleic acid sequence is a NS-specific regulatory element within the scope of the invention.

Cooperating Regulatory Elements

A cooperating regulatory element is any regulatory element that enables another regulatory element to direct expression of a nearby nucleic acid sequence. Typically, cooperating regulatory elements do not direct expression of a nearby nucleic acid sequence by themselves, but rather allow a separate regulatory element, which also does not typically direct expression by itself, to direct expression of a nearby regulatory element. In other words, cooperating regulatory elements can render an inactive regulatory element active. Examples of other regulatory elements that can have their activity enabled by a cooperating regulatory element include, without limitation, ubiquitous and tissue-specific promoters and enhancers such as a NS-specific regulatory element and growth hormone enhancer sequence. Such regulatory elements can be identified by linking a cooperating regulatory element to a potential, inactive regulatory element and testing for the expression of a nearby nucleic acid sequence as described herein. In addition, cooperating regulatory elements can be, for example, mammalian cooperating regulatory elements. A mammalian cooperating regulatory element is any cooperating regulatory element that contains a sequence based upon a sequence from a mammalian genome.

Cooperating regulatory elements can enable another regulatory element to direct expression of a nearby nucleic acid sequence constitutively or transiently. In other words, a cooperating regulatory element can convert a nonfunctional regulatory element into a functional regulatory element either continuously or for a limited time period during an animal's lifetime. Thus, cooperating regulatory elements are not restricted to a particular time period, provided the cooperating regulatory element renders an inactive regulatory element active at, at least, some time during an animal's lifetime.

A cooperating regulatory element can be, without limitation, a nucleic acid sequence identical to or similar to the nucleic acid sequence described in SEQ ID NO:4, provided the nucleic acid sequence functions as a cooperating regulatory element. SEQ ID NO:4 has the following nucleic acid sequence: 5'-AAGGATTTGG AGAAGGG-GAG CTGAATTCAT TTGCTTTTGT CTGTTACCAG CTCTGGGGGC AGAGAGAGAG CCATCCCCTG GGAACAGCCT GAGAATTCCC ACTTCCCCTG AGGAGCCCTC CCTTCTTAG-3'.

Sequences identical to or similar to the sequence described in SEQ ID NO:4 can be identified by sequence alignments and standard hybridization techniques described herein. For example, nucleic acid sequences having at least about 70% sequence identity to the sequence of SEQ ID NO:4 are within the scope of the invention and can be identified by hybridization under conditions of moderate stringency. Further, nucleic acid sequences having at least about 80%, 90%, or 95% sequence identity to the sequence of SEQ ID NO:4 can be identified by high stringency hybridization. Thus, similar nucleic acid sequences can include nucleic acid sequences that are at least about 70%, 78%, 80%, 90%, 95%, 98%, or 99% identical to the sequence described in SEQ ID NO:4. It follows that similar nucleic acid sequences can be identified as any sequence that hybridizes with the sequence described in SEQ ID NO:4 under moderate to high stringency conditions.

In addition, a cooperating regulatory element can be a nucleic acid sequence having a variation of a sequence identical to or similar to the sequence described in SEQ ID NO:4, provided this sequence can function as a cooperating regulatory element. Variations to such sequences can include, without limitation, deletions, insertions, and base substitutions, as well as combinations of deletions, insertions, and base substitutions. Thus, nucleic acid sequences longer and shorter than the sequence described in SEQ ID NO:4 that function as cooperating regulatory elements are within the scope to the invention. For example, sequences that contain a stretch of about four to eight nucleotides that are identical to a stretch found in SEQ ID NO:4 are considered variations of SEQ ID NO:4 and are cooperating regulatory elements provided they function as cooperating regulatory elements. It is noted that, depending on the degree of homology, sequences that are variants of SEQ ID NO:4 can also be similar to SEQ ID NO:4 as defined by, for example, the hybridization conditions above.

Further, a cooperating regulatory element can be any nucleic acid sequence, provided this sequence can function as a cooperating regulatory element. Thus, nucleic acid sequences that function as a cooperating regulatory element and do not contain any sequence homology to the sequence described in SEQ ID NO:4 are considered cooperating regulatory elements within the scope of the invention.

Cooperating regulatory elements lacking homology with SEQ ID NO:4, as well as those that are homologous, can be obtained by chemical synthesis, isolation and cloning from genomic DNA, or other means known in the art, including the use of trap assays and PCR technology carried out using, for example, oligonucleotides corresponding to portions of SEQ ID NO:4.

The following methods can be used to identify nucleic acid sequences that function as cooperating regulatory elements. These nucleic acid sequences can be, as described above, identical or similar to SEQ ID NO:4, a variation of SEQ ID NO:4, or non-homologous to SEQ ID NO:4. Generally, a construct is made to contain a known regulatory element that is inactive by itself, a given nucleic acid sequence to be tested for cooperating regulatory element function, and at least one nearby reporter or marker sequence that can be monitored for expression. This construct is introduced into cells and the expression of the reporter or marker is determined and compared to the expression determined for a similar construct lacking the given nucleic acid sequence. If expression of the reporter or marker sequence driven by the inactive regulatory element is enabled by the presence of the given nucleic acid sequence, then the given nucleic acid sequence is a cooperating regulatory element within the scope of the invention.

Possible reporter and/or marker sequences and methods for introducing nucleic acid into cells are described herein. The expression of the reporter or marker sequence in cells can be determined in vivo, ex vivo, in vitro, and in situ using methods known in the art. For example, the expression of LacZ can be assayed using intact embryos or tissue sections derived from an embryo or organism. In addition, the cells can be in vivo or in vitro. Thus, a construct can be introduced into cells in an organism or into cells in culture. For example, a construct can be introduced into transformed cell lines or primary cultures, and assayed for reporter sequence expression.

The constructs used to identify cooperating regulatory elements can contain additional regulatory elements that do not interfere with the identification of cooperating regulatory element activity. These additional regulatory elements can be, without limitation, promoters, enhancers, and the like. In addition, these additional regulatory elements typically aid in or facilitate the identification of cooperating regulatory elements. For example, a construct containing a given nucleic acid sequence to be tested for cooperating regulatory element function can also contain a minimal promoter sequence, such as a portion of an upstream sequence from the herpes simplex virus ICP4 gene, the TK gene, or a heat shock gene. The additional regulatory element may, by itself, not direct the expression of any nearby nucleic acid sequence.

Typically, a construct containing a known regulatory element that is inactive by itself such as the NS-specific regulatory element having the nucleic acid sequence of SEQ ID NO:3, a given nucleic acid sequence to be tested for cooperating regulatory element function, a minimal promoter sequence such as a portion of an upstream sequence from the herpes simplex virus ICP4 gene, and a reporter sequence such as the LacZ sequence is used to generate transgenic embryos. These transgenic embryos can be made and analyzed as described herein.

The expression of the LacZ sequence by cells can be determined by the visualization of blue staining in whole mount transgenic embryos and histologic sections. Negative controls can include, without limitation, non-transgenic embryos as well as transgenic embryos containing a construct lacking the known regulatory element that is inactive by itself. Positive controls can include, without limitation, transgenic embryos containing a construct that has both the NS-specific regulatory element having the nucleic acid sequence of SEQ ID NO:3 and the cooperating regulatory element having the nucleic acid sequence of SEQ ID NO:4.

If LacZ expression driven by an inactive known regulatory element is determined to be enabled by the presence of the given nucleic acid sequence, then the given nucleic acid sequence is a cooperating regulatory element within the scope of the invention.

Temporal Regulatory Element

A temporal regulatory element is any regulatory element that confers a temporal expression pattern to a nearby nucleic acid sequence. The term "temporal expression pattern" is defined in relation to any other regulatory element, if present, and means that a nearby nucleic acid sequence is expressed for a specific period of time. This temporal expression pattern is not observed if the temporal regulatory element is deleted or otherwise rendered inactive. For example, a transgenic animal containing a construct that contains a temporal regulatory element will express a nearby nucleic acid sequence for a specific period of time whereas a transgenic animal that contains the identical construct lacking the temporal regulatory element does not.

A temporal regulatory element can confer a shorter or longer period of expression than would otherwise occur if the temporal element were absent or rendered inactive. For example, a temporal regulatory element can convert a continuously expressed nucleic acid sequence into a sequence that is expressed for a period of days during development. Likewise, a temporal regulatory element can convert a non-expressed nucleic acid sequence into a sequence that is expressed for a defined, non-continuous period of time.

It is noted that temporal regulatory elements by themselves may not direct the expression of any nearby nucleic acid sequence. Temporal regulatory elements also can function with other regulatory elements to direct nucleic acid expression. Examples of other regulatory elements that can have their activity regulated in a temporal manner by a temporal regulatory element include, without limitation, ubiquitous and tissue-specific promoters and enhancers such as midbrain-specific regulatory elements.

Temporal regulatory elements can be, for example, mammalian temporal regulatory elements. A mammalian temporal regulatory element is any temporal regulatory element that contains a sequence based upon a sequence from a mammalian genome. Temporal regulatory elements also can be temporal tissue-specific regulatory elements such as temporal midbrain-specific regulatory elements and temporal NS-specific regulatory elements.

A temporal regulatory element can be, without limitation, a nucleic acid sequence identical to or similar to the nucleic acid sequence described in SEQ ID NO:5, provided the nucleic acid sequence functions as a temporal regulatory element. SEQ ID NO:5 has the following nucleic acid sequence: 5'-ACTAGTTCCG AATCCCATGT GAACTGATTT CCCTCATCTC CTTCAATCAG CTCCATAGGC CACTGAGGCA GGGCCATGAA CGTTAAGACC TCTGCCCTGA AGAGTTTGTG ATCCTGAGAT GAGGGCTTTA GCCCCAGTCA GTCCTCTGAG GGGAAGGGTC CAGGCAGCTC TGAGGAATGT AACCACTGGC GTTTGAGGTC TGAAAAGGAT TTGGAGAAGG GGAGCTGAAT TCATTTGCTT TTGTCTGTTA CCAGCTCTGG GGGCAGAGAG AGAGCCATCC CCTGGGAACA GCCTGAGAAT TCCCACTTCC CCTGAGGAGC CCTCCCTTCT TAGGCCCTC-3'.

Sequences identical to or similar to the sequence described in SEQ ID NO:5 can be identified by sequence alignments and standard hybridization techniques described herein. For example, nucleic acid sequences having at least about 70% sequence identity to the sequence of SEQ ID NO:5 are within the scope of the invention and can be identified by hybridization under conditions of moderate stringency. Further, nucleic acid sequences having at least about 80%, 90%, or 95% sequence identity to the sequence of SEQ ID NO:5 can be identified by high stringency hybridization. Thus, similar nucleic acid sequences can include nucleic acid sequences that are at least about 70%, 80%, 90%, 95%, 98%, or 99% identical to the sequence described in SEQ ID NO:5. It follows that similar nucleic acid sequences can be identified as any sequence that hybridizes with the sequence described in SEQ ID NO:5 under moderate to high stringency conditions.

In addition, a temporal regulatory element can be a nucleic acid sequence having a variation of a sequence identical to or similar to the sequence described in SEQ ID NO:5, provided this sequence can function as a temporal regulatory element. Variations to such sequences can include, without limitation, deletions, insertions, and base substitutions, as well as combinations of deletions, insertions, and base substitutions. Thus, nucleic acid sequences longer and shorter than the sequence described in SEQ ID NO:5 that function as temporal regulatory elements are within the scope to the invention. For example, sequences that contain a stretch of about four to eight nucleotides that are identical to a stretch found in SEQ ID NO:5 are considered variations of SEQ ID NO:5 and are temporal regulatory elements provided they function as temporal regulatory elements. It is noted that, depending on the degree of homology, sequences that are variants of SEQ ID NO:5 can also be similar to SEQ ID NO:5 as defined by, for example, the hybridization conditions above.

Further, a temporal regulatory element can be any nucleic acid sequence, provided this sequence can function as a temporal regulatory element. Thus, nucleic acid sequences that function as temporal regulatory elements and do not contain any sequence homology to the sequence described in SEQ ID NO:5 are considered temporal regulatory elements within the scope of the invention.

Temporal regulatory elements lacking homology with SEQ ID NO:5, as well as those that are homologous, can be obtained by chemical synthesis, isolation and cloning from genomic DNA, or other means known in the art, including the use of trap assays and PCR technology carried out using, for example, oligonucleotides corresponding to portions of SEQ ID NO:5.

The following methods can be used to identify nucleic acid sequences that function as temporal regulatory elements. These nucleic acid sequences can be, as described above, identical or similar to SEQ ID NO:5, a variation of SEQ ID NO:5, or non-homologous to SEQ ID NO:5. Generally, a construct is made to contain a known regulatory element, a given nucleic acid sequence to be tested for temporal regulatory element function, and at least one nearby reporter or marker sequence that can be monitored for expression. This construct is introduced into cells and the time periods when expression occurs is determined and compared to those determined for a similar construct lacking the given nucleic acid sequence. If the time period for expression changes in any way for the construct containing the given nucleic acid sequence when compared with a similar construct lacking the given nucleic acid sequence, then the given nucleic acid sequence is a temporal regulatory element within the scope of the invention.

Possible reporter and/or marker sequences and methods for introducing nucleic acid into cells are described herein. The expression of the reporter or marker sequence in cells can be determined in vivo, ex vivo, in vitro, and in situ using methods known in the art. For example, the expression of LacZ can be assayed using intact embryos or tissue sections derived from an embryo or organism. In addition, the cells can be in vivo or in vitro. Thus, a construct can be introduced into cells in an organism or into cells in culture. For example, a construct can be introduced into transformed cell lines or primary cultures, and assayed for reporter sequence expression.

The constructs used to identify temporal regulatory elements can contain additional regulatory elements that do not interfere with the identification of temporal regulatory element activity. These additional regulatory elements can be, without limitation, promoters, enhancers, and the like. In addition, these additional regulatory elements typically aid in or facilitate the identification of temporal regulatory elements. For example, a construct containing a given nucleic acid sequence to be tested for temporal regulatory element function can also contain a minimal promoter sequence, such as a portion of an upstream sequence from the herpes simplex virus ICP4 gene, the TK gene, or a heat shock gene. The additional regulatory element may, by itself, not direct the expression of any nearby nucleic acid sequence.

Typically, a construct containing a given nucleic acid sequence to be tested for temporal regulatory element function, a minimal promoter sequence such as a portion of an upstream sequence from the herpes simplex virus ICP4 gene, and a reporter sequence such as the LacZ sequence is used to generate transgenic embryos. These transgenic embryos can be made and analyzed as described herein.

The time period of LacZ expression by cells can be determined by comparing results generated from embryos containing a construct having the given nucleic acid sequence to be tested for temporal regulatory element function with results generated from embryos containing a similar construct lacking the given nucleic acid sequence to be tested for temporal regulatory element function. A control experiment can include comparing the results generated from transgenic embryos containing a construct that has the temporal regulatory element having the nucleic acid sequence of SEQ ID NO:5 with results generated from embryos containing a similar construct lacking this temporal regulatory element.

If the time period of LacZ expression by cells is determined to be changed in any way by the presence of the given nucleic acid sequence, then the given nucleic acid sequence is a temporal regulatory element within the scope of the invention.

Nucleic Acid Constructs

Generally, a nucleic acid construct of the invention contains a selected nucleic acid sequence and at least one of the following regulatory elements: an isolated midbrain-specific regulatory element, an isolated NS-specific regulatory element, an isolated potentiating regulatory element, an isolated cooperating regulatory clement, or an isolated temporal regulatory element. A nucleic acid construct can contain multiple copies of the same isolated regulatory element or multiple copies of different isolated regulatory elements of the same type. For example, a single construct can contain three copies of midbrain-specific regulatory element X in addition to a single copy of both midbrain-specific regulatory element Y and midbrain-specific regulatory element Z. A nucleic acid construct also can contain a combination of different types of isolated regulatory elements. For example, a single nucleic acid construct can contain an isolated NS-specific regulatory element, an isolated potentiating regulatory element, and an isolated cooperating regulatory element.

Nucleic acid constructs can be circular or linear. In addition, nucleic acid constructs can be RNA or DNA, including cDNA, genomic DNA, and synthetic (e.g., chemically synthesized) DNA, and can be double-stranded or single-stranded. Where single-stranded, a nucleic acid construct can be the sense strand or the anti-sense strand. Generally, a nucleic acid construct of the invention is in the form of a plasmid or a linear fragment. Fragments of nucleic acid constructs are also considered within the scope of the invention, and can be produced, for example, by PCR or generated by treatment with one or more restriction endonucleases. RNA constructs can be produced by in vitro transcription.

A nucleic acid construct can exist as a separate molecule (e.g., a DNA fragment produced by PCR or restriction endonuclease treatment) independent of other sequences or be incorporated into a vector, an autonomously replicating plasmid, a virus (e.g., a retrovirus, adenovirus, or herpes virus), or into the genomic DNA of a prokaryote or eukaryote. In addition, a nucleic acid construct can be part of a hybrid or fusion nucleic acid sequence.

A selected nucleic acid sequence can be any nucleic acid sequence. Typically, selected nucleic acid sequences of the invention encode a polypeptide, messenger RNA, transfer RNA, or ribosomal RNA or regulate the expression of a polypeptide, messenger RNA, transfer RNA, or ribosomal RNA. For example, a cDNA that encodes an enzyme or an anti-sense molecule that prevents an enzyme from being expressed can be used. The term "anti-sense molecule" encompasses any nucleic acid sequence that contains sequences that are complementary to the coding strand of a naturally-occurring polypeptide, transfer RNA, or ribosomal RNA, including flanking or intron sequences. Thus, anti-sense oligonucleotides as well as enzymatic nucleic acid molecules that specifically target and cleave RNA by using complementary anti-sense sequences such as ribozymes are considered anti-sense molecules within the scope of the invention. These ribozymes can have any general structure including, without limitation, hairpin, hammerhead, or axhead structures, provided the molecule cleaves RNA.

The polypeptide encoded by a selected nucleic acid sequence can be any synthetically engineered or biologically derived polypeptide. In addition, the polypeptide can be naturally occurring in mammals or heterologous to mammals. Thus, mammalian polypeptides, non-mammalian polypeptides, modified polypeptides, and portions of polypeptides are considered within the scope of the invention. With the current advances in recombinant nucleic acid and nucleic acid sequencing technology, countless nucleic acid sequences are not only known but also readily available from sequence databases such as Genebank®.

Generally, a selected nucleic acid sequence of the invention contains sequences that encode a polypeptide as well as promote the expression of the polypeptide when present in a cell. It is noted that the sequences contained within the selected nucleic acid sequence that promote the expression of a polypeptide should not interfere with the desired function of midbrain-specific, NS-specific, potentiating, cooperating, and/or temporal regulatory elements present on the same nucleic acid construct. For example, if midbrain-specific expression is desired by a particular construct, then a promoter sequence that overrides the midbrain specificity of the midbrain-specific regulatory element should not be used to promote expression. When used, the sequences that promote polypeptide expression are typically regulatory elements that flank the polypeptide encoding sequences.

A selected nucleic acid sequence can contain additional component sequences that may or may not be necessary for the expression of the selected nucleic acid sequence. For example, these additional component sequences can provide a better expression or functioning of the selected nucleic acid sequence by affecting transcription, stability of the mRNA, or the like. Additional component sequences can include, without limitation, introns, enhancers, polyadenylation sequences, a TATA box, and the like. Such components can be included in the selected nucleic acid sequence as desired to obtain the optimal performance of the selected nucleic acid sequence when in a cell.

To determine if a particular combination of components present within a selected nucleic acid sequence functions as desired, the desired target cells can be stably or transiently transformed using methods known in the art with nucleic acid that contains both that particular combination as well as a reporter sequence. At a suitable time after transformation, an assay for expression of the reporter sequence can be performed. One assay, for example, entails identifying the transient expression of LacZ. In this case, a suitable time for conducting the assay is about 1–3 days after introducing the nucleic acid. The use of transient assays is particularly important when using a selected nucleic acid sequence that contains components that have not previously been demonstrated or confirmed as compatible with the desired target cells.

A similar approach can be used to determine if a particular nucleic acid construct containing a selected nucleic acid sequence and at least one regulatory element of the invention functions as desired within a particular target cell.

The regulatory elements and selected nucleic acid sequences can be at any distance from each other as well as in any orientation with relationship to each other, provided the regulatory element functions as desired. For example, a nucleic acid construct can contain a regulatory element that is a few bases or a few hundred kilobases upstream or downstream of a selected nucleic acid sequence.

The methods of constructing selected nucleic acid sequences as well as constructs containing selected nucleic acid sequences and regulatory elements are well known to those skilled in the art. In addition, methods of identifying and isolating suitable nucleic acid components such as promoters, polyadenylation sequences, selectable marker sequences, reporter sequences, enhancers, introns, and the like are well known to those skilled in the art. Generally, these methods involve basic molecular biology and biochemical techniques as described elsewhere (Sambrook J., et al., Molecular Cloning: A Laboratory Manual, 2nd ed., Cold Spring Harbor Laboratory Press (1989)). Further, methods of identifying and isolating nucleic acid sequences that encode a polypeptide are well known to those skilled in the art.

Cells Containing Regulatory Elements

Any cell containing an isolated midbrain-specific regulatory element, an isolated NS-specific regulatory element, an isolated potentiating regulatory element, an isolated cooperating regulatory element, and/or an isolated temporal regulatory element is within the scope of the invention. This includes, without limitation, prokaryotic and eukaryotic cells that contain a nucleic acid construct having an isolated midbrain-specific regulatory element, an isolated NS-specific regulatory element, an isolated potentiating regulatory element, an isolated cooperating regulatory element, and/or an isolated temporal regulatory element. It is noted that cells containing these constructs are not required to express them. In addition, the isolated regulatory element can be integrated into the genome of the cell or maintained in an episomal state. Thus, cells can be stably or transiently transfected with a construct containing an isolated regulatory element of the invention.

Methods of introducing a nucleic acid, such as those that produce or contain an isolated midbrain-specific regulatory element, an isolated NS-specific regulatory element, an isolated potentiating regulatory element, an isolated cooperating regulatory element, and/or an isolated temporal regulatory element, into a cell, whether in vivo or in vitro, are well known to those skilled in the art. For example, calcium phosphate precipitation, electroporation, heat shock, lipofection, microinjection, and viral-mediated nucleic acid transfer are common methods of introducing nucleic acid into cells. In addition, naked DNA can be delivered directly to cells in vivo as describe elsewhere (U.S. Pat. No. 5,580,859 and U.S. Pat. No. 5,589,466 including continuations thereof). Further, nucleic acid can be introduced into cells by generating transgenic animals as described herein.

Methods of identifying cells that contain an isolated regulatory element of the invention are also well known to those skilled in the art. Such methods include, without limitation, PCR and nucleic acid hybridization techniques such as Northern and Southern analysis. In some cases, immunohistochemistry and biochemical techniques can be used to determine if a cell contains a particular nucleic acid sequence by detecting the expression of molecules encoded by that particular sequence. For example, a nucleic acid construct can contain a potentiating regulatory element and a selected nucleic acid sequence that encodes an enzyme. If the expression of that particular enzyme is detected after transfection with that construct in a cell that normally does not express that enzyme, then that cell contains the selected nucleic acid sequence that encodes the enzyme and, in most cases, the potentiating regulatory element.

Animals Containing Regulatory Elements

Any animal containing a nucleic acid that produces or contains an isolated midbrain-specific regulatory element, an isolated NS-specific regulatory element, an isolated potentiating regulatory element, an isolated cooperating regulatory element, and/or an isolated temporal regulatory element is within the scope of the invention. This includes, without limitation, aquatic animals (such as fish, sharks, dolphin, and the like), farm animals (such as pigs, goats, sheep, cows, horses, rabbits, and the like), rodents (such as rats, guinea pigs, and mice), primates (such as baboon, monkeys, chimpanzees, and humans), and domestic animals (such as dogs and cats) that contain a nucleic acid construct having an isolated midbrain-specific regulatory element, an isolated NS-specific regulatory element, an isolated potentiating regulatory element, an isolated cooperating regulatory element, and/or an isolated temporal regulatory element. It is noted that animals containing these constructs are not required to express them. In addition, the isolated regulatory element can be integrated into the genome of the animal or maintained in an episomal state. Thus, animals can be stably or transiently transformed with an isolated regulatory element of the invention. Further, the isolated regulatory element can be in all the cells of the animal as well as in some, but not all of the cells. That is, the invention provides for mosaic animals. The isolated regulatory element can be integrated as a single copy or in concatamers, e.g., head-to-head tandems or head-to-tail tandems.

Methods of introducing a nucleic acid that produces or contains an isolated midbrain-specific regulatory element, an isolated NS-specific regulatory element, an isolated potentiating regulatory element, an isolated cooperating regulatory element, and/or an isolated temporal regulatory element into an animal are well known to those skilled in the art. For example, naked DNA can be delivered directly to cells in vivo as describe elsewhere (e.g., U.S. Pat. No. 5,580,859 and U.S. Pat. No. 5,589,466). In addition, viral-mediated nucleic acid transfer techniques can be used to deliver nucleic acid into cells of an animal. Viral-mediated vectors for delivering nucleic acid in vivo can include, without limitation, RNA viral vectors derived from, for example, retroviruses and DNA viral vectors derived from, for example, adenoviruses, vaccinia viruses, and herpes viruses. Further, nucleic acid can be introduced into cells by generating transgenic animals as described herein.

Methods of identifying animals that contain an isolated regulatory of the invention are also well known to those skilled in the art. Such methods include, without limitation, PCR and nucleic acid hybridization techniques such as Northern and Southern analysis. In some cases, immunohistochemistry and biochemical techniques can be used to determine if an animal has cells that contain a particular nucleic acid sequence by detecting the expression of molecules encoded by that particular sequence. For example, a nucleic acid construct can contain a potentiating regulatory element and a selected nucleic acid sequence that encodes an enzyme. If the expression of that particular enzyme is detected after transfection in a cell derived from an animal that normally does not express that enzyme, then that animal contains the selected nucleic acid sequence that encodes the enzyme and, in most cases, the potentiating regulatory element.

Any selected nucleic acid sequence can be expressed in a tissue-specific manner in an animal by using a midbrain-specific or NS-specific regulatory element described herein. Thus, any animal can be given a selected nucleic acid sequence that is expressed in either a midbrain-specific or NS-specific manner. Generally, a nucleic acid construct containing a selected nucleic acid sequence and, at least, an isolated midbrain-specific or an isolated NS-specific regulatory element is administered to an animal. Possible methods for administering nucleic acid to cells in vivo are described herein.

Any selected nucleic acid sequence can be expressed in a temporal manner in an animal by using a temporal regulatory element described herein. Thus, any animal can be given a selected nucleic acid sequence that is expressed for a specific period of time. Generally, a nucleic acid construct containing a selected nucleic acid sequence and, at least, an isolated temporal regulatory element is administered to an animal. Possible methods for administering nucleic acid to cells in vivo are described herein.

The invention will be further described in the following examples, which do not limit the scope of the invention described in the claims.

EXAMPLES

Example 1

General methods

The second intron of the rat nestin gene was studied extensively to determine the molecular mechanisms involved in regulating nucleic acid expression. Specifically, a comprehensive set of fragments of the 1.8 kb second intron of the rat nestin gene was constructed and each fragment analyzed for the ability to confer tissue-specific expression of a LacZ reporter gene in transgenic embryos.

Constructs 1–20

A 4.0 kb EcoRI/XhoI fragment containing the LacZ gene with 142 bp of the herpes simplex virus ICP4 gene promoter (Yaworsky PJ et al., *J. Biol. Chem.* 272:25112–25120 (1997)) was end-filled and ligated into an EcoRV opened pSafyre vector (Bogarad, unpublished) to form pLacZ. This minimal promoter-LacZ arrangement in pLacZ was used to generate the subsequent plasmids containing portions of the second intron of nestin gene.

A 1.85 kb BstYI fragment from the plasmid pNesIx (obtained from Dr. A. McMahon; Harvard University, Cambridge, Mass.) corresponding to the second intron of the rat nestin gene was ligated into the BamHI site of pLacZ. The forward orientation of the insert was confirmed by restriction mapping. This plasmid contains the entire second intron of the rat nestin gene upstream of the minimal promoter-LacZ arrangement (Construct 1).

Eighteen fragments having deletions within the second intron of the rat nestin gene were generated either by restriction endonuclease digestion or by the polymerase chain reaction (PCR). In cases where PCR was used, primers were designed to contain 16 nucleotides of nestin intron sequence. To facilitate directional cloning into the pLacZ plasmid, the PCR primers incorporated restriction enzyme sites. The 5' primers all contained an XbaI site while the 3' primers had a PstI site. All primers contained two random bases at the 5' end for optimal restriction digest of the amplified product. Identical PCR conditions were used to generate each fragment (28 cycles: 94° C. for 30 seconds; 62° C. for 1 minute; and 72° C. for 30 second with 5 minute first and last cycles at 94° C. and 72° C., respectively).

Each fragment was then cloned into pLacZ and sequenced to confirm the wild-type sequence. These plasmids contain constructs numbered 2 through 19 with the beginning and end base positions of each deletion fragment being indicated in FIG. 1. The solid dark line in FIG. 1 represents the nestin second intron sequence with the indicated numbering for Constructs 1–19 and for Construct 20 being identical to the sequence entries in GenBank under accession numbers AF004334 (rat) and AF004335 (human), respectively. The open box schematically represents the minimal promoter-LacZ arrangement. The four triangles represent the four DNA regulatory elements identified herein: A, midbrain-specific regulatory element; B, potentiating regulatory element; C, cooperating regulatory element; and D, NS-specific regulatory element. Each construct is in the 5'-3' orientation unless indicated otherwise by an arrow (Constructs 8 and 12).

A fragment containing the second intron from the human nestin gene was amplified from human genomic DNA by PCR using primers 5'-AATCTAGACCTGGAGGTGGCCAACG-3' (SEQ ID NO:9) and 5'-AACTGCAGAGTTCTCAGCCTCCAGG-3' (SEQ ID NO:10) that anneal in the coding region of the human nestin gene flanking the second intron (Dahlstrand J et al., *J. Cell Sci.* 103:589–597 (1992)). These primers also provide XbaI and PstI restriction sites. Cycling conditions were as follows: 94° C. for 30 seconds, 60° C. for 1 minute, and 72° C. for 1 minute for 35 cycles with a 5 minute initial denaturation step at 94° C. and a final 5 minute extension at 72° C. A 1.73 kb amplification product was agarose gel purified (Qiagen, Chatsworth, Calif.) and cloned into the pCRScript vector (Stratagene, La Jolla, Calif.) to form a new plasmid called pflNes. The plasmid, pHNes, was digested with XbaI and PstI, which generated a short deletion from the 3'-end of the intron, and ligated into pLacZ creating a plasmid containing Construct 20. Construct 20 contains 1605 bp of the second intron from the human nestin gene (FIG. 1).

DNA Sequence Analysis

The 1.85 kb BstYI fragment from the plasmid pNesIx and the 1.73 kb fragment of pHNes were used to sequence the second intron from the rat and human nestin genes, respectively. Automated DNA sequencing was performed on an Applied Biosystems 373A DNA Sequencer (ABI, Foster City, Calif.). Primers were specifically designed to provide sequence from both DNA strands. Subsequent analyses were carried out using the Bestfit program of the University of Wisconsin Genetics Computer Group (Madison, Wis.) software or the Complign program of McMolly Tetra 3.5 (Soft Gene GmbH, Berlin) with minimal match length set at 10, mismatches set at 0, and gap penalty set at 3.

Generation and Identification of Transgenic Embryos

Plasmids containing constructs 1–20 were treated with restriction endonucleases to generate DNA fragments containing each construct as indicated in FIG. 1. For some constructs, restriction endonucleases that do not produce blunt ends were used. In addition, some constructs contained polylinker sequences. The fragments corresponding to each construct were isolated by agarose gel electrophoresis and purified over Qiagen columns. The purified DNA was diluted to a final concentration of 2.0 $\mu$g/ml in a TE buffer (10 mM Tris-C1 pH 7.3; 0.25 mM EDTA) for microinjection. FVB mice were used as donors for microinjection and CD-1 mice were used as foster mothers following standard protocols of Hogan B et al. (Cold Spring Harbor, N.Y.: Cold Spring Harbor Laboratory Press) (1994). To identify transgenic embryos, genomic DNA was isolated from the yolk sac of each embryo and tested for the presence of the LacZ transgene by PCR using primers specific for the LacZ transgene, 5'-GACGGGTTGTTACTCGCTCAC-3' (SEQ ID NO:7) and 5'-GCGTGTACCACAGCGGATGGT-3' (SEQ ID NO:8). These primers amplify a 868 bp product corresponding to the LacZ transgene after 35 cycles (94° C. for 30 seconds, 62° C. for 1 minute, and 72° C. for 30 seconds with an initial denaturation step at 94° C. for 5 minutes and a final extension step at 72° C. for 5 minutes).

The number of embryos isolated and examined for enhancer activity at 10.5 dpc is indicated in FIG. 1 with the transgene positive column depicting the number of these embryos carrying the LacZ transgene as determined by PCR screening of yolk sac DNA. Central nervous system β-galactosidase activity was divided into two categories: either full CNS staining (marked under the column "throughout") or midbrain staining (under the column "MB"). Embryos that stained outside of the nervous system were scored as ectopic. The asterisk under the "MB" column with Construct 12 indicates that although the midbrain stained in one embryo, staining was also present at non-specific sites such as the heart, limbs, skin, and additional neural tissue and was thus scored as ectopic.

Embryo Isolation and β-galactosidase Staining

Embryos were isolated at various developmental stages with the morning of the microinjection designed as 0.5 dpc (days post coitum). Embryos were fixed in 4% paraformaldehyde in PBS at 4° C. for 2 hours at 10.5 dpc and for 3 hours at 13.5 dpc. The fixative was removed with three 15 minute washes at 37° C. in a buffer of 100 mM $NaH_2PO_4$ (pH 7.3), 2 mM $MgCl_2$, 0.1% deoxycholate, and 0.2% NP-40. Staining proceeded in the same buffer supplemented with 5mM $K_3Fe(CN)_6 \cdot 3H_2O$, 5 mM $K_4Fe(CN)_6$, and 1 mg/ml X-gal. Staining was monitored after 1 hour and allowed to proceed overnight. The reaction was stopped by rinsing with PBS and post-fixing the embryos in 4% paraformaldehyde/0.25% glutaraldehyde in PBS for 4 hours at 4° C. Embryos were dehydrated in 70% ethanol and photographed on a Leica Stereo Zoom M3Z microscope. Consistently, three staining patterns emerged for the whole mount staining as depicted in FIG. 2: positive for the entire developing CNS (Panels A, B, and G–I), positive for the ventral midbrain only (Panels D–F), and negative for the neuroepithelium (Panel C).

Histologic sections were obtained by embedding the embryos in paraffin wax followed by microtome sectioning at 10 $\mu$m thickness. Sections were analyzed and photographed with a Leica DMRB microscope.

Immunohistochemistry on Tissue Sections

Embryos were isolated at 10.5 dpc in ice-cold PBS, fixed for 3 hours in 4% paraformaldehyde in PBS, embedded in paraffin wax, and microtome cross-sectioned at a thickness of 10 $\mu$m. Immunohistochemical staining was carried out using the Vectastain Elite ABC Kit and Vector DAB Substrate Kit (Vector Laboratories, Burlingame, Calif.). The anti-rat-nestin primary antibody (Clone Rat-401, Pharmingen, San Diego, Calif.) was used at a concentration of 5 $\mu$g/ml and the anti-proliferating-cell-nuclear-antigen (Clone PC10, Boehringer Mannheim, Indianapolis, Ind.) was used at 50 $\mu$g/ml. The proliferating-cell-nuclear-antigen is a marker for dividing cells. No staining was observed in the absence of primary antibody. The sections were counter stained briefly with hematoxylin and photographed on a Leica DMRB microscope.

Statistical Analysis

Statistical independence was established using the chi-squared test. In cases where any expected frequency was less than 5, the Fisher exact test was used.

Example 2

Midbrain-specific regulatory element

Construct 1 contains a 1.85 kb DNA fragment corresponding to the full 1670 bp of the second intron of the nestin gene. Transgenic embryos containing Construct 1 exhibited LacZ expression exclusively within the developing CNS at 10.5 dpc (FIG. 2, Panel A). Intense β-galactosidase activity was detected in the telencephalon, diencephalon, mesencephalon, metencephalon, myelencephalon, and spinal cord. Ventral spinal cord staining progressed along the entire anterior-posterior axis of the embryo except at the most posterior portions of the spinal cord. Dorsal regions of the telencephalon did not stain, and in the spinal cord, dorsal staining was found only in regions anterior to the forelimb buds.

Transgenic embryos containing either Construct 7 or Construct 8 (bases 1068 through 1406 in forward and reverse orientation, respectively) did not exhibit the full staining pattern observed in transgenic embryos containing Construct 1 but rather exhibited a developing midbrain-specific staining pattern (FIG. 2, panel D). Only cells of the mesencephalon expressed the transgene with a concentration of staining localized in more ventral regions (FIG. 2, panel D). Thus, the 339 bp DNA sequence from bases 1068 through 1406 of the second intron of the nestin gene contains a midbrain-specific regulatory element. In addition, identical β-galactosidase expression patterns were observed for transgenic embryos containing either Construct 7 or Construct 8, confirming that the activity of the midbrain-specific regulatory element contained within these constructs is not dependant on orientation. Thus, the midbrain-specific regulatory element contained within Constructs 7 and 8 functions as a true enhancer.

Five additional constructs that overlap this 339 bp fragment were analyzed. Constructs 9 and 10 contained fragments representing the last and first two-thirds of the 339 bp fragment, respectively. Construct 9 was unable to specifically direct transgene expression to the nervous system (not shown). Construct 10, however, produced LacZ transgene expression in the developing mesencephalon, narrowing the relevant DNA region down to 204 bp (FIG. 2, Panel E). Interestingly, the dorsal extension of stained cells along the midbrain-hindbrain border previously observed with the Construct 8 embryos (FIG. 2, Panel D) was not seen in every midbrain-stained embryo (compare with FIG. 2, Panel E), possibly due to variability in development maturity. Attempts to shorten the relevant DNA region even further proved inconclusive.

Three out of 43 transgenic embryos containing Construct 11 exhibited a midbrain-specific expression pattern (FIG. 2, Panel F), with an additional 7 transgenic embryos displaying independent and different ectopic staining patterns (not shown). This low frequency of midbrain-specific staining (7.0%) compared with the frequency of midbrain-specific staining observed with Constructs 7, 8, and 10, combined, (38%) suggested that either the midbrain-specific regulatory element did not reside on the Construct 11 fragment or that the 123 bp midbrain-specific regulatory element was too weak to overcome DNA integration effects in the transgenic embryos. Alternatively, the spacing of the enhancer relative to the minimal promoter may have been suboptimal to allow consistent expression of enhancer activity. To test the latter possibility, a construct with 3 copies of the 123 bp DNA fragment, Construct 12, was constructed placing the sequence at varying distances from the transcription start site. None of the 4 transgenic embryos obtained with this multimerized fragment (Construct 12) displayed specific staining in the midbrain (not shown).

To formally exclude that the midbrain-specific regulatory element resides between bases 1190 and 1199 (gap between Constructs 9 and 11), Construct 13 was generated. No midbrain-specific expression was observed in these transgenic embryos (not shown). Thus, the DNA sequence between bases 1068 and 1271 of the second intron of the nestin gene contains a midbrain-specific regulatory element as positively demonstrated with Construct 10 (FIG. 2, Panel E). This midbrain-specific regulatory element is represented as a triangle (labeled A) in FIG. 1. As demonstrated in Example 2, a potentiating regulatory element is necessary for the activity of this particular midbrain-specific regulatory element.

Example 3

Potentiating regulatory element

Statistical analysis was performed on the data generated from the large number of transgenic embryos studied. These results suggested the presence of a general transcriptional potentiator regulatory element that is necessary for efficient activity of the particular midbrain-specific regulatory element described in Example 1. In the case of Construct 9 (bases 1200–1406), 5 of 16 (31%) transgenic embryos exhibited intense β-galactosidase activity at ectopic sites in completely independent staining patterns (FIG. 1). This high frequency of ectopic staining (31% as compared to 7%, 16 out of 222, for all other constructs combined, $p=0.008$) indicated the presence of a regulatory element that alone possesses no tissue specificity, but enables transcriptional activity when under the influence of another tissue-specific regulatory element. Indeed, reproducible midbrain-specific expression was detectable only with constructs that harbored the putative transcriptional potentiator regulatory element (Constructs 7–10; FIG. 1). Thus, the DNA fragment corresponding to bases 1200 through 1271 contains a potentiating regulatory element based on the ratio of LacZ expressing embryos (specific or ectopic) to total transgenic embryos.

A further refinement, based on Constructs 7–19, narrowed the potentiating regulatory element between bases 1200–1255. Specifically, Constructs 7–10, all of which contain bases 1200–1271, yielded 20 out of 50 embryos (40%) that had specific or ectopic LacZ expression. In addition, Constructs 14–16, containing bases 1200–1255, produced 15 out of 20 (75%) LacZ expressing embryos. In contrast, constructs lacking bases 1200–1271 had low numbers of embryos with β-galactosidase activity. For example, Constructs 11–13 generated only 15 out of 69 (22%, $p=0.031$) stained embryos while Constructs 17–19 yielded 10 out of 39 (26%, $p=0.0003$) stained embryos. This statistical analysis of LacZ expression indicates the presence of a potentiating regulatory element between bases 1200 and 1255. Taken together, these results demonstrate that tissue-specific regulatory activity in the midbrain was achieved through the interaction/potentiation of regulatory elements, namely a midbrain-specific regulatory element between 1068 and 1190 (FIG. 1, triangle A) and a potentiating regulatory element between 1200 and 1255 (FIG. 1, triangle B).

Comparing data from transgenic embryos containing Constructs 16 and 17 indicated that the potentiating regulatory element located between 1200 and 1255 augments NS-specific expression. Thus, potentiating regulatory elements are not limited to potentiating expression in midbrain tissue, indicating that potentiating regulatory elements can potentiate expression with any tissue-specific regulatory element.

Example 4

NS-specific and Cooperating regulatory elements

Deleting large regions of the second intron of the nestin gene revealed that the NS-specific regulatory element resides downstream of base 1069 (FIG. 1, Constructs 2–4). Transgenic embryos containing Construct 4 exhibited a pattern of staining identical to that observed with the full 1.85 kb fragment (compare Panels A and B of FIG. 2). As observed with Construct 1, β-galactosidase staining was reduced slightly in the most posterior portion of the ventral spinal cord. In addition, staining in the dorsal spinal cord was weak, even at anterior levels. In the developing brain, staining was restricted by boundaries between the telencephalon and the diencephalon and between the mesencephalon and the metencephalon. The staining pattern from Construct 3 was identical to that of both Constructs 1 and 4 (not shown). Construct 2 lacks the 3' region of the intron and could not confer LacZ expression to the developing CNS (not shown). These results suggested that the NS-specific regulatory element resides between bases 1069 and 1850, in the 3' region of the intron.

To further refine the location of the NS-specific regulatory element, Constructs 5 and 6 were generated to contain shorter 3' regions of the intron. Neither construct produced LacZ transgene expression within the developing nervous system (FIG. 2, Panel C), suggesting that the relevant NS-specific regulatory element resides within the 333 bp region between base 1069 and base 1401. Constructs 7 and 8, however, contain bases 1069 through 1406 and cause midbrain-specific expression, not NS-specific expression.

The identification of a midbrain-specific regulatory element and a potentiating regulatory element between bases 1068 and 1255 indicates that at least one other NS-specific regulatory element in the nestin intron is responsible for the staining pattern observed with Construct 4 (FIG. 2, Panel B). Further, the NS-specific regulatory element(s) must be located between bases 1401 and 1850 since NS-specific expression was observed with Construct 4 (FIG. 2, Panel B), yet Constructs 7 and 8 were only active in the midbrain (FIG. 2, Panel D). The results from transgenic embryos containing Constructs 5 and 6 indicate that the most 3' region of the nestin intron is unable to drive expression independent of sequences between 1069 and 1401 (FIG. 2, Panel C). Thus, expression in regions beyond the midbrain required the interaction of sequences in the 1068–1406 fragment with those in the 1406–1850 fragment.

In order to identify the regulatory elements responsible for this interaction, deletions from the 3' end of the intron were generated. Constructs 14 and 15 produced staining patterns that were identical to each other and indistinguishable from those obtained from Construct 4 (FIG. 2, Panel G). These results suggested that the regulatory element conferring NS-specific expression must reside between bases 1401 and 1587.

To test if the midbrain-specific and potentiating regulatory elements (1068–1255) were required for the entire NS expression pattern, three additional constructs containing deletions from the 5' end through the 1068–1272 region were generated. Constructs 16, 17, and 18 were all able to generate reproducibly the original expression pattern observed with Construct 4 (not shown). From these results, it was concluded that elements between bases 1272 and 1400 interact with elements between bases 1401 and 1587 to produce the original pattern of gene expression observed with the intact intron. Further, results from transgenic embryos containing Construct 18 demonstrated that the original NS-specific expression was achieved in the absence of the midbrain-specific and potentiating regulatory elements. Results from an additional construct containing a deletion from the 3' end to base 1477 (Construct 19) indicated that a 206 bp fragment could reproducibly generate the full nestin intron staining pattern (FIG. 2, Panel H). Taken together, these results indicate the existence of two regulatory elements, one between bases 1272 and 1400 (triangle C in FIG. 1) and another between bases 1401 and 1477 (triangle D in FIG. 1).

Comparing the results generated from Constructs 9 and 16 demonstrates that the regulatory element between bases 1401 and 1477 confers NS-specific expression. Thus, the DNA sequence between bases 1401 and 1477 is a NS-specific regulatory element. Likewise, the comparison of results from Construct 5 with the results from Constructs 17–19 demonstrates that the regulatory element between bases 1272 and 1400 cooperates with the tissue-specific regulatory element to enable tissue-specific expression. Thus, the DNA sequence between bases 1272 and 1400 is a cooperating regulatory element.

Example 5

Human NS-specific regulatory element

The second intron from the human nestin gene was cloned and analyzed for regulatory element activity in transgenic embryos to determine if the human nestin gene intron contains the same regulatory elements as the rat nestin gene intron. A 1.7 kb human clone contained 21 bp of exon 2, the complete 1687 bp of intron 2, and 23 bp of exon 3. Based on the identification of regulatory elements in the rat intron, Construct 20 was generated to included the first 1584 bp of human intron sequence (FIG. 1). Five of seven transgenic embryos exhibited intense β-galactosidase staining throughout the entire CNS (FIG. 2, Panel I). The expression pattern was similar to that previously observed with the rat enhancer with either Constructs 1, 4, or 19 (FIG. 2, Panels A, B, and H, respectively). These experiments demonstrated that the second intron from the human nestin gene also possesses NS-specific regulatory elements thereby revealing functional conservation of these intron regulatory elements during evolution.

Example 6

Sequence analysis

Figure 4A:
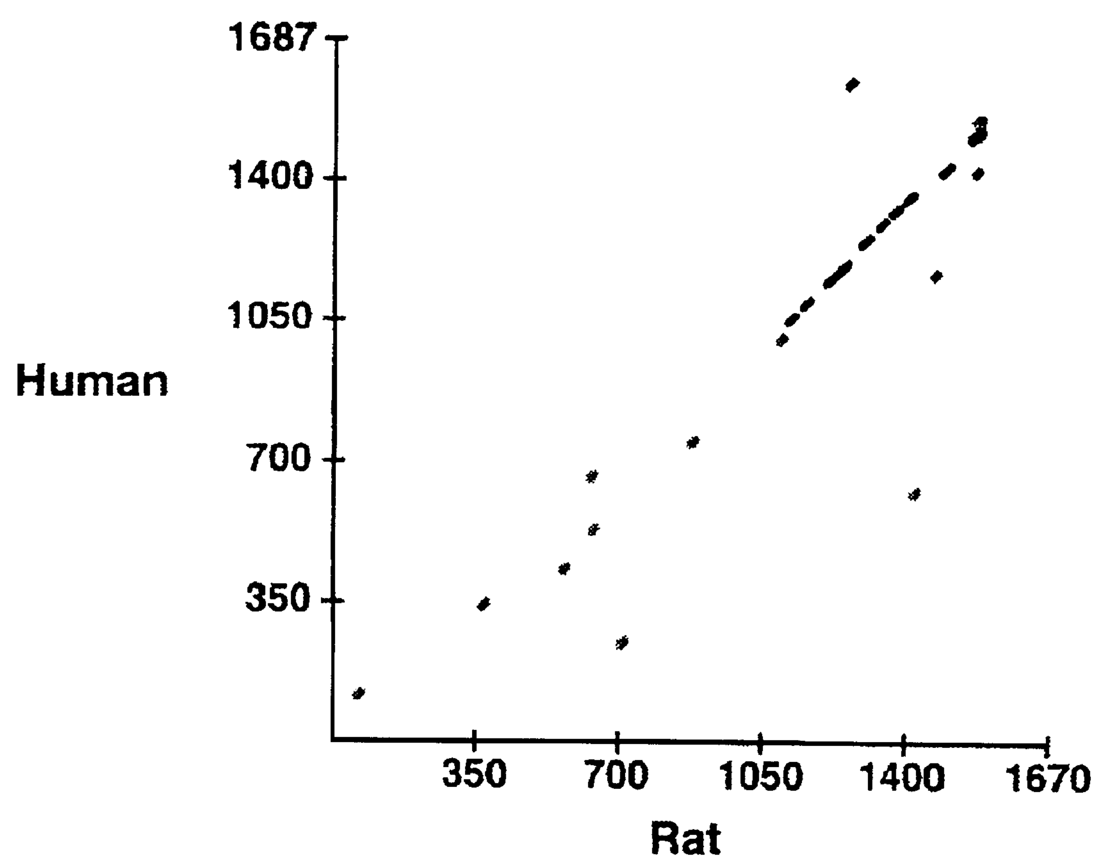
FIG. 4 is diagram depicting the sequence conservation in the second intron of the rat and human nestin gene. Panel A is a graph depicting the comparison between the two intron sequences. Sequence identities are shaded, and putative transcription factor binding sites are underlined and labeled. The numbering is identical to the intron sequences deposited in GenBank under accession numbers AF004334 (rat) and AF004335 (human).
Figure 5A:
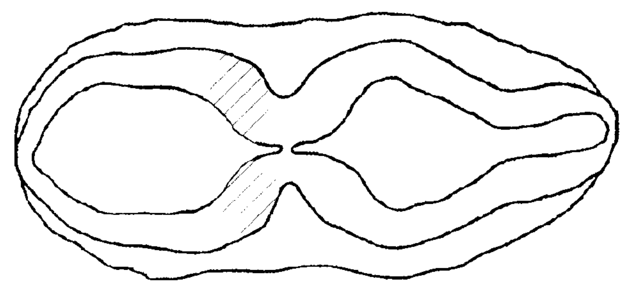
FIG. 5 is a schematic diagram of a transverse section through the third and fourth ventricles of a 10.5 dpc embryo representing a model of neural stem cell heterogeneity. Dorsal is on the right. Panel A represents expression conferred by the midbrain-specific regulatory element, Panel B represents expression conferred by the NS-specific regulatory element, and Panel C represents endogenous nestin polypeptide expression. The comparison identifies three populations of NS stem cells: the first is nestin$^{(pos)}$/NS-specific regulatory clement$^{(neg)}$/Midbrain-specific regulatory element$^{(neg)}$, the second is nestin$^{(pos)}$/NS-specific regulatory element$^{(neg)}$/midbrain-specific regulatory element $^{(pos)}$, and the third is nestin$^{(pos)}$/NS-specific regulatory element$^{(pos)}$/midbrain-specific regulatory element$^{(pos)}$.
Figure 5B:
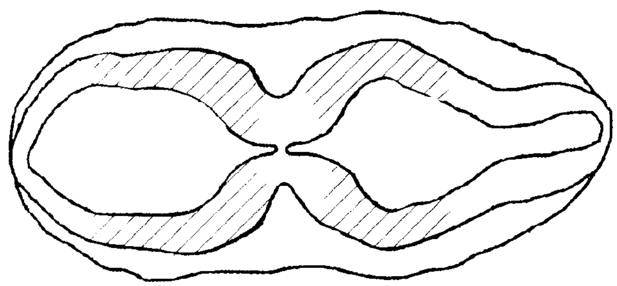
Figure 5C:
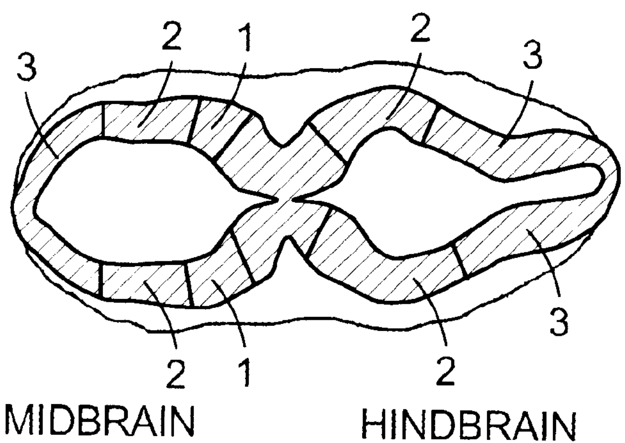

In addition to the functional analyses in transgenic mice, the second intron of both the rat and human nestin genes were sequenced. The rat intron contained 1670 bp while the human contained 1687 bp. Both sequences had no overall similarities to sequences in the databases. A comparison between the two sequences revealed a highly divergent 5' region and a clustering of conserved regions in the 3' end of the intron resulting in 37% total similarity (FIG. 4, Panel A). The stretches of sequence conservation exactly coincided with regions of the intron for which the midbrain-specific, potentiating, NS-specific, and cooperating regulatory elements were demonstrated. Specifically, the 132 bp midbrain-specific regulatory element and the 56 bp potentiating regulatory element are 61.0% and 70.4% identical between rat and human, respectively (FIG. 4, Panel B). The 77 bp NS-specific regulatory element and the 129 bp cooperating regulatory element are 83.1% and 78.2% identical (FIG. 4, Panel C). These percentages were calculated using an alignment program that includes gaps. If gaps are excluded, these values increase.

Few consensus sequences for putative transcription factor binding were present in the regulatory element regions. Two putative retinoid-X receptor beta (RXR-β) half-site consensus sequences (Marks MC et al., *EMBO J.* 11:1419–1435

(1992)) were conserved: one in the midbrain-specific regulatory element at base 1154 of the rat (base 1029 in human) and another in the NS-specific regulatory element at base 1469 in the rat (1373 in human). In addition, the cooperating regulatory element and the NS-specific regulatory element each contain a putative POU-domain transcription factor binding site that was conserved in both species: a Pit-1 binding site (Peers B et al., *Mol. Cell Biol.* 10:4690–4700 (1990)) at base 1292 in rat (1187 in human) and a POU-class III binding site (Li P et al., *Genes Dev.* 7:2483–2496 (1993)) at base 1435 in rat (1339 in human). This high degree of sequence similarity and the conservation of putative transcription factor binding sites in regions having regulatory element activity indicates that similar regulatory mechanisms control nestin expression in both rat and human. Moreover, these results indicate that rat and human sequences from the second intron of the nestin gene can be used interchangeably as regulatory elements including midbrain-specific, potentiating, NS-specific, cooperating, and temporal regulatory elements.

Example 7

Figure 3K:
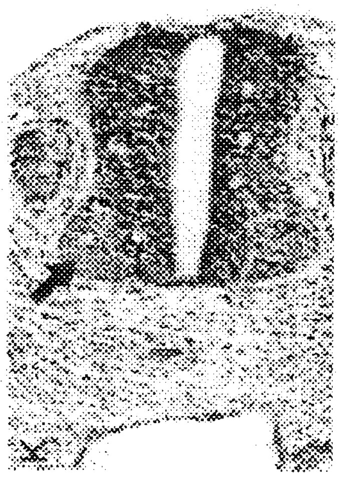
Figure 3J:
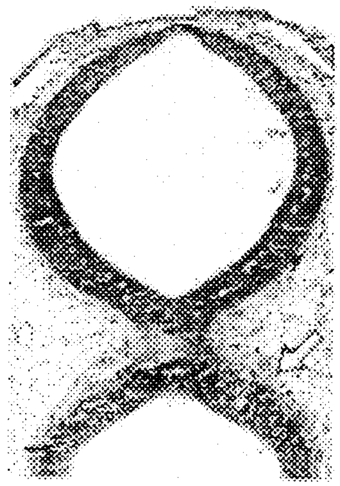

Cell localization of expression Sections through a transgenic embryo containing Construct 1 confirmed that all of the β-galactosidase activity was restricted to the developing nervous system. In the hindbrain, an intense ventrally localized stripe of expression was visible around the 4th ventricle (FIG. 3, Panel A). Staining was also observed in lateral stripes around the 3rd ventricle of the ventral midbrain. The anterior spinal cord of these embryos exhibited β-galactosidase activity in both ventral and dorsal cells, however, the dorsal-most regions of the spinal cord were consistently negative (FIG. 3, Panel B). The staining in ventral regions was intense and predominantly localized to ventricular cells with activity being detected along the pial surface as well. Floor plate cells and the notochord did not stain. In the more posterior region of the spinal cord, the staining became more restricted to ventral, ventricular cells (FIG. 3, Panel C).

The cellular localization of β-galactosidase activity was identical between Constructs 1 and 4 (compare FIG. 3, Panels A and D). Sections through transgenic embryos containing Construct 8, however, confirmed that only ventral cells of the midbrain were stained (FIG. 3, Panel E). Positive cells were present bilaterally, on each side of the 3rd ventricle, in tegmental neuroepithelial cells. In contrast, transgenic embryos containing Construct 19 (cooperating and NS-specific regulatory elements) exhibited stripes of staining in both the hindbrain and midbrain similar to the expression pattern observed with Constructs 1 and 4 (compare FIG. 3, Panels A, D, and F). Staining in the anterior spinal cord was also similar although the intensity of staining was weak dorsally (FIG. 3, Panel G). Also in the anterior spinal cord, regulatory element activity was observed in both ventral and dorsal cells with strong ventricular cell localization (B, G, H). Staining becomes more ventrally restricted in posterior spinal cord (C, I). These experiments demonstrate that 206 bp fragment between bases 1271 and 1477 contains all of the spatial and temporal regulatory elements (cooperating and NS-specific regulatory elements) necessary to reproduce the full expression pattern observed in transgenic embryos containing Construct 1.

Interestingly, the regulatory elements from the human nestin gene exhibited the strongest expression of β-galactosidase activity observed. Sections through the anterior spinal cord of these embryos displayed intense β-galactosidase activity throughout the entire dorsal-ventral axis of the spinal cord (FIG. 3, Panel H). The notochord and floor plate cells were again negative for staining. The posterior spinal cord of these embryos was strongly stained, however, as observed with previous constructs, the dorsal-most region of the spinal cord was only weakly positive (FIG. 3, Panel I). Taken together, these data revealed that only cells in the developing nervous system were targeted by the identified regulatory elements, although not every neuroepithelial cell exhibited expression at this developmental stage.

Example 8

Nestin polypeptide expression

Using monoclonal antibody against nestin, nestin polypeptide expression was compared to the expression observed using the identified regulatory elements. While the expression conferred from the regulatory elements observed strict boundaries (FIG. 3, Panels A–I), the immunohistochemical detection of nestin polypeptide revealed a broader expression pattern. In the hindbrain and midbrain, nestin polypeptide immunoreactivity was detected throughout the entire dorsal/ventral axis (FIG. 3, Panel J) unlike the striped expression observed in transgenic embryos containing Construct 1 (entire second intron) or Construct 19 (cooperating and NS-specific regulatory elements). In the spinal cord, nestin polypeptide expression was detected both in ventral and dorsal cells (FIG. 3, Panel K) but it was absent in post-mitotic regions of the ventral horns where presumptive motor neurons are differentiating (black arrow FIG. 3, Panel K) as reported previously (Frederiksen K and RDG McKay, *J. Neurosci.* 8:1144–1151 (1988); Zimmerman LB et al., *Neuron* 12:11–24 (1994)). Interestingly, the notochord was weakly immunopositive yet none of the constructs containing regulatory elements were active in this region. Immunoreactivity was also detected in dorsal root ganglia and endothelial walls of blood vessels and some axonal projections were detected by regulatory element activity (FIG. 3, Panel I) and by nestin polypeptide detection (FIG. 3, Panel K). The more extensive expression of nestin polypeptide indicated that additional DNA regulatory elements, residing outside the second intron, participate in the regulation of the endogenous nestin gene locus.

The broad expression pattern of nestin polypeptide at 10.5 dpc indicated that NS stem cells could be subdivided into at least three populations: nestin-positive cells that activate the midbrain-specific regulatory element, nestin-positive cells that activate the NS-specific regulatory element, and nestin-positive cells that do not activate either the midbrain-specific or the NS-specific regulatory element. This was most apparent when FIG. 3, Panels A and D–F were compared with FIG. 3, Panel E. Transgenic embryos containing Constructs 1, 4, 8, and 19 exhibited expression in the midbrain tegmental neuroepithelial cells in the very same location (indicated with a white arrow). Although cells in the midbrain exhibited LacZ expression in transgenic embryos containing Construct 8, other NS stem cells were unable to activate this fragment. This observation suggested that these ventral midbrain neural stem cells are different from other NS stem cells, such as spinal cord stem cells. Similarly, in the spinal cord, ventral cells expressed the LacZ transgene when presented with the NS-specific and cooperating regulatory elements while dorsal cells did not. Thus, molecular differences were evident by the capability of various cell populations to activate different nestin regulatory elements at a given time point. These data provide molecular evidence that neural stem cells are heterogeneous cell populations based on differences in their transcription factor repertoires. Thus, the isolation of nestin regulatory elements in transgenic mice reveals a molecular heterogeneity in neural stem cells that is not apparent with either in situ hybridization or immunohistochemical approaches.

Example 9

Temporal regulatory element

Tissue was isolated at various developmental stages from transgenic animals containing Construct 8 (midbrain-specific, potentiating, and cooperating regulatory elements in reverse orientation) and Construct 16 (potentiating, cooperating, and NS-specific regulatory elements) and assayed for β-galactosidase activity. The total number of embryos examined and the number of LacZ transgene positive embryos (as detected by PCR) are presented in Table I. Briefly, transgenic embryos containing Construct 8 exhibited β-galactosidase activity in the midbrain region only at 10.5 dpc (Table I) but not at the later developmental stages tested. These data indicated that the midbrain neuroepithelial cells that expressed the transgene at 10.5 dpc are a unique subpopulation of neural stem cells that possess a distinct complement of transcription factors. Such molecular differences enable transient enhancer activity in these specific cells for a short period of time prior to terminal neuronal differentiation. In contrast, transgenic embryos containing Construct 16 or the human construct (Construct 20) exhibited β-galactosidase activity in NS stem cells at later developmental stages (Table I).

The striking frequency of ectopically-stained embryos from Construct 8 at developmental stages later than 10.5 dpc indicates the presence of a general transcriptional potentiator in this fragment. In the absence of an active midbrain-specific regulatory element (down regulation of midbrain-specific regulatory activity), an increased frequency of transcriptional activity at ectopic sites was obtained. Specifically, 14 ectopically-stained embryos out of 34 transgenic embryos (41%) were obtained as compared to 21 out of 2597 (8%) for all other constructs ($p<0.0001$).

TABLE I

Temporal regulation of regulatory elements.

| | | | | CNS | | |
|---|---|---|---|---|---|---|
| Construct | Stage (dpc) | Number of Embryos | Transgene Positive | Through-out | Mid-brain | Ec-topic |
| 8 | 9.5 | 7 | 2 | | 0 | 0 |
| | 10.5 | 73 | 18 | | 8 | 0 |
| | 11.5 | 34 | 3 | | 0 | 3 |
| | 12.5 | 37 | 8 | | 0 | 2 |
| | 13.5 | 126 | 21 | | 0 | 9 |
| 16 | 10.5 | 43 | 10 | 8 | | 0 |
| | 13.5 | 69 | 8 | 2 | | 0 |
| | 17.5 | 32 | 6 | 2 | | 0 |
| 20 | 10.5 | 21 | 7 | 5 | | 0 |
| | 13.5 | 33 | 5 | 4 | | 0 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid construct comprising an isolated nucleic acid and a selected nucleic acid sequence, wherein said isolated nucleic acid comprises a midbrain-specific regulatory element and is 339 or fewer bases in length, said midbrain-specific regulatory element having a sequence present in a rat or human nestin gene.

2. The nucleic acid construct of claim 1, wherein said selected nucleic acid sequence encodes a polypeptide.

3. The nucleic acid construct of claim 1, wherein said construct further comprises a potentiating regulatory element.

4. The nucleic acid construct of claim 3, wherein said potentiating regulatory element comprises the nucleic acid sequence of SEQ ID NO:2.

5. The nucleic acid construct of claim 1, wherein said isolated nucleic acid comprises the nucleic acid sequence of SEQ ID NO:1.

6. A nucleic acid construct comprising an isolated nucleic acid and a selected nucleic acid sequence, wherein said isolated nucleic acid comprises a potentiating regulatory element and is 616 or fewer bases in length, said potentiating regulatory element having a sequence present in a rat or human nestin gene.

7. The nucleic acid construct of claim 6, wherein said selected nucleic acid sequence encodes a polypeptide.

8. The nucleic acid construct of claim 6, wherein said isolated nucleic acid comprises the nucleic acid sequence of SEQ ID NO:2.

9. A nucleic acid construct comprising an isolated nucleic acid and a selected nucleic acid sequence, wherein said isolated nucleic acid comprises a cooperating regulatory element and is 616 or fewer bases in length, said cooperating regulatory element having a sequence present in a rat or human nestin gene.

10. The nucleic acid construct of claim 9, wherein said selected nucleic acid sequence encodes a polypeptide.

11. The nucleic acid construct of claim 9, wherein said isolated nucleic acid comprises the nucleic acid sequence of SEQ ID NO:4.

12. A nucleic acid construct comprising an isolated nucleic acid and a selected nucleic acid sequence, wherein said isolated nucleic acid comprises a temporal midbrain-specific regulatory element and is 339 or fewer bases in length, said temporal midbrain-specific regulatory element having a sequence present in a rat or human nestin gene.

13. An isolated cell comprising the nucleic acid construct of claim 1, 6, 9, or 12.

14. The cell of claim 13, wherein said cell is eukaryotic.

15. The cell of claim 14, wherein said eukaryotic cell is mammalian.

16. The nucleic acid construct of claim 12, wherein said selected nucleic acid sequence encodes a polypeptide.

17. The nucleic acid construct of claim 12, wherein said isolated nucleic acid comprises the nucleic acid sequence of SEQ ID NO:5.

* * * * *

SEQUENCE LISTING

```
<160> NUMBER OF SEQ ID NOS: 12

<210> SEQ ID NO 1
<211> LENGTH: 132
<212> TYPE: DNA
<213> ORGANISM: Rattus
<220> FEATURE:

<400> SEQUENCE: 1

actagttccg aatcccatgt gaactgattt ccctcatctc cttcaatcag ctccataggc     60

cactgaggca gggccatgaa cgttaagacc tctgccctga agagtttgtg atcctgagat    120

gagggcttta gc                                                        132


<210> SEQ ID NO 2
<211> LENGTH: 56
<212> TYPE: DNA
<213> ORGANISM: Rattus
<220> FEATURE:

<400> SEQUENCE: 2

cccagtcagt cctctgaggg gaagggtcca ggcagctctg aggaatgtaa ccactg         56


<210> SEQ ID NO 3
<211> LENGTH: 77
<212> TYPE: DNA
<213> ORGANISM: Rattus
<220> FEATURE:

<400> SEQUENCE: 3
```

```
gccctccaga tggtagtgtg gacaaaaggc aataattagc atgagaatcg gcctccctcc     60

cagaggatga ggtcatc                                                     77


<210> SEQ ID NO 4
<211> LENGTH: 129
<212> TYPE: DNA
<213> ORGANISM: Rattus
<220> FEATURE:

<400> SEQUENCE: 4

aaggatttgg agaaggggag ctgaattcat ttgcttttgt ctgttaccag ctctgggggc     60

agagagagag ccatcccctg ggaacagcct gagaattccc acttcccctg aggagccctc    120

ccttcttag                                                            129


<210> SEQ ID NO 5
<211> LENGTH: 339
<212> TYPE: DNA
<213> ORGANISM: Rattus
<220> FEATURE:

<400> SEQUENCE: 5

actagttccg aatcccatgt gaactgattt ccctcatctc cttcaatcag ctccataggc     60

cactgaggca gggccatgaa cgttaagacc tctgccctga agagtttgtg atcctgagat    120

gagggcttta gccccagtca gtcctctgag gggaagggtc caggcagctc tgaggaatgt    180

aaccactggc gtttgaggtc tgaaaaggat ttggagaagg ggagctgaat tcatttgctt    240

ttgtctgtta ccagctctgg gggcagagag agagccatcc cctgggaaca gcctgagaat    300

tcccacttcc cctgaggagc cctcccttct taggccctc                           339


<210> SEQ ID NO 6
<211> LENGTH: 206
<212> TYPE: DNA
<213> ORGANISM: Rattus
<220> FEATURE:

<400> SEQUENCE: 6

aaggatttgg agaaggggag ctgaattcat ttgcttttgt ctgttaccag ctctgggggc     60

agagagagag ccatcccctg ggaacagcct gagaattccc acttcccctg aggagccctc    120

ccttcttagg ccctccagat ggtagtgtgg acaaaaggca ataattagca tgagaatcgg    180

cctccctccc agaggatgag gtcatc                                         206


<210> SEQ ID NO 7
<211> LENGTH: 21
<212> TYPE: DNA
<213> ORGANISM: LacZ transgene primer
<220> FEATURE:

<400> SEQUENCE: 7

gacgggttgt tactcgctca c                                               21


<210> SEQ ID NO 8
<211> LENGTH: 21
<212> TYPE: DNA
<213> ORGANISM: LacZ transgene primer
<220> FEATURE:

<400> SEQUENCE: 8

gcgtgtacca cagcggatgg t                                               21
```

-continued

```
<210> SEQ ID NO 9
<211> LENGTH: 25
<212> TYPE: DNA
<213> ORGANISM: Homo sapien
<220> FEATURE:

<400> SEQUENCE: 9

aatctagacc tggaggtggc caacg                                        25


<210> SEQ ID NO 10
<211> LENGTH: 25
<212> TYPE: DNA
<213> ORGANISM: Homo sapien

<400> SEQUENCE: 10

aactgcagag ttctcagcct ccagg                                        25


<210> SEQ ID NO 11
<211> LENGTH: 410
<212> TYPE: DNA
<213> ORGANISM: Rattus

<400> SEQUENCE: 11

actagttccg aatcccatgt gaactgattt ccctcatctc cttcaatcag ctccataggc    60

cactgaggca gggccatgaa cgttaagacc tctgccctga agagtttgtg atcctgagat   120

gagggcttta gccccagtca gtcctctgag gggaagggtc caggcagctc tgaggaatgt   180

aaccactggc gtttgaggtc tgaaaaggat ttggagaagg ggagctgaat tcatttgctt   240

ttgtctgtta ccagctctgg gggcagagag agagccatcc cctgggaaca gcctgagaat   300

tcccacttcc cctgaggagc cctcccttct taggccctcc agatggtagt gtggacaaaa   360

ggcaataatt agcatgagaa tcggcctccc tcccagagga tgaggtcatc              410


<210> SEQ ID NO 12
<211> LENGTH: 442
<212> TYPE: DNA
<213> ORGANISM: Homo sapien

<400> SEQUENCE: 12

agcagctgct catcctaagt tattgaattg attggtccct gctcccctct ttggttcaag    60

gggcgctgag gaaggggcct ggacacaaag acctctgtgc cccgaagagc ttgggatcca   120

gagtgcttag agatcctgag atgagggccc tgacccccag tgaagccacc gaggggaagg   180

gtctggtggg ccccgaggaa tttaactgct attttttgag gcatgaaaag gatttggaga   240

gggggagctg aattcatttg cttttgtctg tcgctagctc tgggggccac cggggaagga   300

ggagggagcc catcccatgg gaacggcctg agaattccca cttccccaga atcctctcct   360

tctcagaccc tccagatggt ggcttggaca atggcagcaa ttagcatgag aatcggtccc   420

ccacacagag gatgaggtca tt                                            442
```